US009163270B2

(12) United States Patent
Corsa et al.

(10) Patent No.: US 9,163,270 B2
(45) Date of Patent: Oct. 20, 2015

(54) **PROCESS FOR THE PRODUCTION OF HYALURONIC ACID IN *ESCHERICHIA COLI* OR *BACILLUS MEGATERIUM***

(75) Inventors: Vincenza Corsa, Abano Terme (IT); Alessandro Negro, Padiva (IT); Sonia Bisicchia, Abano Terme (IT)

(73) Assignee: FIDIA FARMACEUTICI S.P.A., Abano Terme (IT)

( * ) Notice: Subject to any disclaimer, the term of this patent is extended or adjusted under 35 U.S.C. 154(b) by 0 days.

(21) Appl. No.: 13/821,953

(22) PCT Filed: Sep. 9, 2011

(86) PCT No.: PCT/EP2011/065641
§ 371 (c)(1),
(2), (4) Date: Apr. 15, 2013

(87) PCT Pub. No.: WO2012/032153
PCT Pub. Date: Mar. 15, 2012

(65) Prior Publication Data
US 2014/0099673 A1    Apr. 10, 2014

(30) Foreign Application Priority Data
Sep. 9, 2010  (IT) .............. MI2010A1641

(51) Int. Cl.
| | |
|---|---|
| *C12P 19/26* | (2006.01) |
| *C12N 9/52* | (2006.01) |
| *C12N 15/70* | (2006.01) |
| *C08B 37/08* | (2006.01) |
| *C12N 9/04* | (2006.01) |
| *C12N 9/10* | (2006.01) |
| *C12N 9/12* | (2006.01) |
| *C12N 9/92* | (2006.01) |
| *C12N 15/75* | (2006.01) |

(52) U.S. Cl.
CPC ............ *C12P 19/26* (2013.01); *C08B 37/0072* (2013.01); *C12N 9/0006* (2013.01); *C12N 9/1051* (2013.01); *C12N 9/1241* (2013.01); *C12N 9/92* (2013.01); *C12N 15/75* (2013.01); *C12Y 101/01022* (2013.01); *C12Y 204/01212* (2013.01); *C12Y 207/07009* (2013.01); *C12Y 503/01009* (2013.01)

(58) Field of Classification Search
CPC .......... C12P 19/26; C12N 9/52; C12N 15/70; C12N 15/75; C12N 15/52; C12Y 1/00
USPC .................................................. 435/137, 234
See application file for complete search history.

(56) References Cited

U.S. PATENT DOCUMENTS

| | | | | |
|---|---|---|---|---|
| 5,955,310 | A  * | 9/1999 | Widner et al. ............... | 435/69.1 |
| 7,811,806 | B2 * | 10/2010 | Sloma et al. .............. | 435/252.31 |
| 2003/0175902 | A1 | 9/2003 | Sloma et al. | |

OTHER PUBLICATIONS

Dougherty et al. 1993; Molecular characterization of hasB from an operon required for hyaluronic acid synthesis in Group A Steptococci. JBC. 268(10): 7118-7124.*
Crater et al. 1995; Molecular characterization of hasC from an operon required for hyaluronic acid synthesis in Group A streptococci. JBC. 270(48): 28676-28680.*
Mathur et al. 2005; Biochemical characterization of recombinant phsphoglucose isomerase of *Mycobacterium tuberculosis*. Biochem Biophs Res Commun. 337:626-632.*
Duenas et al. 1999; Synthesis of eukaryotic virus proein ina prokaryotic viral-cell system: production of adenovirus type 2 fiber shaft fragment by a tightly regulated T7POL-M13 expression system. J. Virological Methods. 79: 121-131.*
Yu, H. et al., "Metabolic engineering of *Escherichia coli* for biosynthesis of hyaluronic acid," Metabolic Engineering, Academic Press, US, Dec. 24, 2007, vol. 10, No. 1, pp. 24-32.
Widner, B. et al., "Hyaluronic acid production in *Bacillus subtilis*," Applied and Environmental Microbiology, American Society for Microbiology, US, Jul. 1, 2005, vol. 71, No. 1, pp. 3747-3752.
Mao, Z. et al., "A recombinant *E. coil* bioprocess for hyaluronan synthesis," Applied Microbiology and Biotechnology, Springer, Berlin, DE, Mar. 24, 2009, vol. 84, No. 1, pp. 63-69.
Gamer, M. et al., "A T7 RNA polymerase-dependent gene expression system for *Bacillus megaterium*," Applied Microbiology and Biotechnology, Springer, Berlin, DE, Mar. 24, 2009, vol. 62, No. 6, pp. 1195-1203.
Studier, F. W. et al., "Use of T7 RNA polymerase to direct expression of cloned genes," Methods in Enzymology, Academic Press Inc, San Diego, CA, US, Jan. 1, 1990, vol. 185, pp. 60-89.
Chien, L. et al., "Enhanced hyaluronic acid production in *Bacillus subtilis* by coexpressing bacterial hemoglobin," Biotechnology Progress, Sep. 2007, vol. 23, No. 5, pp. 1017-1022.
Kang, Y. et al., "One step engineering of T7-expression strains for protein production: Increasing the host-range of the T7-expression system," Protein Expression and Purification, Academic Press, San Diego, CA, US, Sep. 8, 2007, vol. 55, No. 2, pp. 325-333.

* cited by examiner

*Primary Examiner* — Karen Cochrane Carlson
(74) *Attorney, Agent, or Firm* — Birch, Stewart, Kolasch & Birch, LLP

(57) ABSTRACT

A method of producing hyaluronic acid (HA) in *Escherichia coli* and *Bacillus megaterium* through episomal plasmid vectors wherein the gene is under the control of strong promoter T7, preferably under the control of strong promoter T7 of bacteriophage T7, and a system for the selection of stable bacterial strains producing high levels of hyaluronic acid, are provided.

18 Claims, 6 Drawing Sheets

PROCESS FOR THE PRODUCTION OF HYALURONIC ACID IN ESCHERICHIA COLI OR BACILLUS MEGATERIUM

This application is the National Phase Under 35 U.S.C. §371 of PCT International Application No. PCT/EP2011/065641 which has an International filing date of Sep. 9, 2011, which claims priority to Italian Patent Application No. MI2010A001641 filed on Sep. 9, 2010. The entire contents of all applications listed above are hereby incorporated by reference.

SUBJECT OF THE INVENTION

The present invention discloses a process for the production of hyaluronic acid (HA) in *Escherichia coli* and *Bacillus megaterium* through episomal plasmid vectors wherein the gene is under the control of a strong T7 promoter, preferably under the control of a strong T7 promoter of bacteriophage T7, and a system for the selection of stable bacterial strains producing high levels of hyaluronic acid.

FIELD OF INVENTION

Hyaluronic acid is a natural linear polysaccharide which consists of alternating β-1-4 D-glucuronic acid and β-1-3 N-acetyl glucosamine. Hyaluronic acid is part of the glycosaminoglycan family, and can reach a molecular weight of $10^7$ Da, with approx. 300000 repeating saccharide units. It is widely distributed in the connective tissue and extracellular matrix in the epithelium of eukaryotic organisms, where it is located on the cell surface, but can also be synthesised in some prokaryotic organisms, such as those of the *Streptococcus* family. Glycosaminoglycans are ideal joint lubricants, but also perform many other functional roles in tissue repair, cell motility, adhesion and development, cancer and angiogenesis. Products based on hyaluronic acid have been developed on the basis of these important characteristics, and are used in orthopaedics, rheumatology and dermatology.

The most common natural sources of HA include rooster combs, the classic material from which HA is extracted, and some bacteria, especially those belonging to the *Streptococcus* family. All these different sources present numerous disadvantages: hyaluronic acid obtained from rooster combs can, for example, cause allergies in humans because it is of avian origin, while HA from bacterial sources must be free of all the toxins normally present in those bacteria which can cause possibly serious immune/inflammatory reactions. The current industrial HA purification processes therefore comprise many different steps, with a consequent increase in the final costs of manufacturing the raw material.

There is consequently a strongly felt need for alternative sources that eliminate all the adverse events described, while maintaining reasonable manufacturing costs. In recent years, biosynthesis pathways for the synthesis of hyaluronic acid have been included in detail in numerous organisms. While the genes required for hyaluronic acid synthesis which are present in eukaryotic organisms are distributed throughout the genome, in bacterial systems said genes are often present and organised in operons. For example, in *Streptococcus equi* the operon for hyaluronic acid comprises 5 genes: hasA, hasB, hasC, hasD and hasE. Sometimes, however, the genes are present in two operons: in *Streptcoccus equisimilis* one operon with genes hasA, hasB and hasC is present, and another with genes hasC, hasD and hasE. The genes homologous with hasB, hasC, hasD and hasE of the Streptococci are present in many organisms, and synthesise the enzymes necessary for the synthesis of hyaluronic acid precursors D-glucuronic acid and N acetyl-D glucosamine, which are also the essential constituents of the bacterial walls. In the case of streptococci, hyaluronan synthase (hasA, which is present in the plasma membrane) is the key enzyme for the final synthesis of hyaluronic acid because it performs two functions: it catalyses the union of D-glucuronic acid and N-acetyl-D-glucosamine, and transports the chain of newly-formed hyaluronic acid out of the cell. The study of the enzymes responsible for hyaluronic acid synthesis has allowed the development of recombinant systems in various organisms, such as *Bacillus subtilis, Lactococcus lactis, Escherichia coli* and *Agrobacterium radiobacter*. The first organism engineered to produce hyaluronic acid was *B. subtilis*, through cloning in its chromosome of an operon that carries the hasA gene from *Streptococcus* (which is missing in *Bacillus*), with the tuaD and gtaB genes of *Bacillus* (corresponding to hasB and hasC of *Streptococcus*), under the control of a constitutive promoter (US2003/175902). In this way a biosynthesis pathway was organised in operons similar to those of *Streptococcus equi*, one of the major natural producers of hyaluronic acid. However, the system thus perfected leads to the industrial production of a hyaluronic acid with a weight average molecular weight of less than 1 MDA, with very low manufacturing yields.

The system of expression of hyaluronic acid according to the present invention uses bacteria of the strains *Bacillus Megaterium* and *Escherichia coli*.

*Bacillus Megaterium* is an aerobic gram-positive bacterium, which was described over 100 years ago. Its large size (1 μm, i.e. 100 times larger than *E. coli* in both vegetative and spore-forming form) has made it very popular for morphological analysis studies. This bacterium can contain many different types of plasmids; the plasmid DNA can be transferred by protoplast transformation obtained by treatment with polyethylene glycol, and they all work extremely well, with excellent structural stability. The bacterium can be transduced with phages, and the frequency of transformation can reach $10^6$ transformants per μg of DNA. Several hundred mutants are currently available, which cover various biosynthesis pathways: catabolism, division, sporulation, germination, antibiotic resistance and recombination.

No less than seven plasmids have been found in different strains of *B. megaterium*, with sizes ranging from 5.4 to 165 kb. The genomes of two strains (DSM319:EMBL, accession number CP001983, and QM B1551:EMBL, accession number CP001982) and those of the seven natural plasmids are now available. Although it is considered to be a bacterium present in soil, *B. megaterium* has been found in various ecological niches such as dried meat, seawater and fish. *B. megaterium* is able to grow in various carbon sources, including slaughter waste and industrial syrups with a broad spectrum of sugars (62 of the 95 tested), which include carboxylic acids like acetate. *B. megaterium* can be cultured at high density, up to 80 g of dry weight per liter. Considerable knowledge has been obtained of various recombinant enzymes with different industrial applications which can be secreted in this organism, such as α-amylase, β-amylase, penicillin amidase, neutral protease and β-glucanase. Particularly important are amylases, used in the bread-making industry, glucose dehydrogenase, used industrially for the production of NADH and as a biosensor, and penicillin amidase, used to generate new synthetic antibiotics. Finally, *B. megaterium* is the major source of vitamin B12.

DETAILED DESCRIPTION OF THE INVENTION

The present invention discloses and claims a process for the production of hyaluronic acid (HA) in high industrial yields in *Bacillus megaterium* and *Escherichia coli* through episomal plasmid vectors wherein the genes for the synthesis of the enzymes required for HA production, are under the control of the strong T7 promoter, preferably under the control of the strong T7 promoter of bacteriophage T7, and a system for the selection of engineered, stable bacterial strains producing high amounts of hyaluronic acid having well defined weight average molecular weights (in the following also indicated as MW).

In order to produce recombinant proteins (in this case the enzymatic proteins required for the synthesis of HA) efficiently, systems which use highly controllable strong promoters need to be designed. The invention discloses a process for the transformation of the above-disclosed bacteria, using a very efficient system for the control of the transcription of the genes introduced, as the gene of interest is placed under the control of the promoter dependent on T7 RNA polymerase.

During construction in *E. coli* of the vectors expressing hyaluronic acid in the form of plasmids, it was discovered that the genes thus introduced (which are responsible for synthesis of the hyaluronic acid-producing enzymes) are cell-toxic when their transduction control is a strong constitutive promoter. In fact, in *E. coli* transformed with genes hasA and tuaD, gene transduction of hasA alone leads to a great reduction in the D-glucuronic acid precursors required to constitute the bacterial wall, with the result that the cell dies, whereas gene transduction of tuaD alone generates uncontrolled synthesis of D-glucuronic acid which, by acidifying the bacterium and depriving it of glucose (its precursor), causes its death. Conversely, the transduction of both genes by bacterial polymerases leads to the activation of the two enzymes at different times, because they require different construction times with different procedures and sites of action (for example, hasA is a transmembrane protein with different domains crossing it, so a much longer time is needed for its synthesis and correct folding). The cell can only survive if balanced quantities of the precursor enzymes and the enzyme necessary for hyaluronic acid synthesis are present. In this case, the excess D-glucuronic acid, which is toxic at high levels in the cell, is used by hyaluronan synthase (hasA) which, combining it with glucosamine, incorporates it in the nascent hyaluronic acid and exports it from the cell, thus keeping the cell alive.

Consequently, although both hasA and tuaD are necessary for the synthesis of hyaluronic acid, it is essential for the two genes to work in concert, leaving the cell the time required to:
 produce D-glucuronic acid at non-toxic levels and
 trigger the transcription of the hasA gene in such a way that the latter is able to dispose of the high levels of D-glucuronic acid as they accumulate in the cell.

In the present invention, the problems described above have been solved by
 placing the plasmid genes, necessary for the synthesis of the above disclosed enzymes, under the control of a T7 promoter, preferably under the control of the T7 promoter of bacteriophage T7, dependent on T7 RNA polymerase, which uses repressor XylR in *B. megaterium* (and lac in *E. coli*) for its induction. The T7 promoter of bacteriophage T7 is dependent on the presence of T7 polymerase, so the HA synthesis genes placed under its control can only be transcribed by T7 RNA polymerase, not by the action of the polymerases naturally present in the bacterium;
 perfecting a system of selection of stable, engineered and secreting *B. megaterium* strains and *E. Coli* strains, preferably of viable, engineered and secreting *B. megaterium* strains, wherein the enzymes necessary for the HA synthesis, are present in "balanced" amounts, thus non toxic for the cell.

It is therefore object of the present invention a process for the preparation of hyaluronic acid in *Escherichia coli* or *Bacillus megaterium*, preferably in *B. megaterium*, comprising the following steps:
 (a) culture of bacterial host cells of *Escherichia coli* or *Bacillus megaterium*, preferably of host cells of *B. megaterium*, transformed in a stable way with the T7 RNA polymerase system under conditions suitable for the production of hyaluronic acid in the presence of isopropyl-β-thio-galactopyranoside (IPTG) or xylose respectively as inductors, wherein said bacterial host cells are characterised by being further transformed with:
  (i) at least one episomal plasmid vector comprising a sequence coding for the enzyme hyaluronan synthase and a sequence coding for the enzyme UDP-glucose dehydrogenase in tandem under the control of the strong inducible T7 promoter, preferably under the control of the T7 promoter of bacteriophage T7; or
  (ii) at least one episomal plasmid vector comprising a sequence coding for the enzyme hyaluronate synthase, a sequence coding for the enzyme UDP-glucose dehydrogenase, a sequence coding for the enzyme UDP-glucose pyrophosphorylase and a sequence coding for the enzyme glucose 6 phosphate isomerase, under the control of the strong inducible T7, preferably under the control of the T7 promoter of bacteriophage T7;
 (b) recovery of hyaluronic acid from the culture medium,
wherein such bacterial host cells of *Escherichia coli* or *Bacillus megaterium* transformed in a stable way with the T7 RNA polymerase system and with plasmid vector (i) or (ii) able to produce hyaluronic acid of step a) are pre-selected in the plate on IPTG or xylose gradient respectively.

The Applicant preferably used *B. megaterium* (preferably pertaining to QMB1551 or DSM319 strains), transformed with the T7 RNA polymerase system, for its subsequent transformation with the episomal plasmid containing the genes for HA synthesis, as it presents various advantages as host for the expression of heterologous DNA:
 the HA produced is easily secreted;
 it is free of exotoxins and endotoxins, unlike gram-negative bacteria;
 it does not contain any alkaline protease, and consequently does not induce the breakdown of the protein produced;
 it is structurally very stable by comparison with recombinant plasmids: *B. megaterium* can contain a much larger number of episomal plasmids than *Bacillus Subtilis*, which are more stable; *B. megaterium* can also support much larger inserts than *E. coli* and *B. subtilis*, and this characteristic is very important when, as in the case of the present invention, a long metabolic pathway like that of hyaluronic acid is to be engineered.

The T7 RNA polymerase system transferred to *B. megaterium* (and to *E. coli*, preferably to *E. coli* BL21 DE3 strain) controls the expression of the genes responsible for synthesis of the HA biosynthesis pathway (cloned in episomal plasmids), and guarantees
 very high activity and selectivity of gene transcription;
 a consequent very high production of the recombinant proteins required for the synthesis of hyaluronic acid.

The final yield of the desired product will be very high: much higher than that obtained with *B. subtilis*, where the operon system is cloned on the chromosome of the bacterium, and is under the control of non-inducible constitutive promoters.

In fact, the T7 RNA polymerase system described above is inducible: it is introduced artificially into the bacterium and activated by the Applicant by adding substances like IPTG (for *E. coli* in quantities of between 0.1 mM and 10 mM, preferably between 0.4 and 1 mM) or xylose (for *B. Megaterium* in quantities of between 0.1% and 10%, preferably between 0.5% and 1% w/v); in their presence, the inducer bonds to the repressor, modifying its configuration, and the repressor then detaches from the promoter, allowing the polymerases of the bacterium to transduce the gene for synthesis of T7 RNA polymerase. The latter, in turn, can only activate the gene transcription of the genes placed under the control of a T7 promoter. In this way the synthesis of the whole biosynthesis process for the production of HA can be controlled. The system is so efficient in that a single polymerase is dedicated to the gene of interest, and the RNA polymerase of the bacterium is not involved. With this methodology, the cell protein synthesis system is saturated, so that the proteins of interest are obtained in amounts to 50% or more of the total proteins.

Further, as demonstrated in the following by the Applicant, by modulating the fermentation times, the Applicant can obtain the production of high amounts of HA with specific weight average molecular weights, comprised in a range of from 100 KD to above 2 MD. More particularly, when the process according to the invention uses bacterial host cells of *B. megaterium* and fermentation time is comprised of from 80 to 160 hours, it is possible to obtain HA having a weight average MW comprised in the range 100-500 KD; when fermentation time is comprised of from 40 to 80 hours, it is possible to obtain HA having a weight average MW comprised in the range 500-1000 KD; when fermentation time is comprised of from 12 to 40 hours, it is possible to obtain HA having a weight average MW comprised in the range $1 \times 10^6$-$3 \times 10^6$ D.

In a preferred embodiment of the present invention, the sequence coding for the enzyme hyaluronan synthase (hasA) is obtained from a *Streptococcus* strain, preferably from *Streptococcus zooepidemicus*, and the sequences coding for enzymes UDP-glucose dehydrogenase (hasB or tuaD), UDP-glucose pyrophosphorylase (hasC or gtaB) and glucose 6 phosphate isomerase (hasE or pgi), are derived from *B. subtilis*.

According to a particularly preferred embodiment of the present invention, the sequences coding for enzymes hyaluronan synthase, UDP-glucose dehydrogenase, UDP-glucose pyrophosphorylase and glucose 6 phosphate isomerase include an upstream Shine-Dalgarno sequence.

Even more preferably, said plasmid vector (i) comprises or consists of the nucleotide sequence as defined in SEQ ID NO:1 or in SEQ ID NO:2.

The subsequent purification of the HA secreted will be extremely simple, with the result that the industrial production process will be much cheaper than the process according to the state of the art.

Specifically, *E. coli* strains BL21 DE3 (Stratagene, Calif., USA) have T7 RNA polymerase cloned in the chromosome of the bacterium under the control of the inducible promoter lac. It can be induced with IPTG for the transcription of the T7 RNA polymerase gene. At this point, the T7 RNA polymerase produced can transcribe the genes under its control.

A similar system has also been engineered in *B. megaterium*. In this case the system uses two plasmids: the first leads to the synthesis of the enzymatic protein T7 RNA polymerase, and the second (engineered) to that of the messenger of the gene (or genes) of interest, under the control of the T7 promoter of bacteriophage T7. The first plasmid, pT7-RNAP (MoBiTec), derives from plasmid pBM100 264 (MoBiTec), which replicates in *B. megaterium* QM B1551 (MoBiTec) and also contains the replication origin of *E. coli*, resistance to ampicillin and chloramphenicol and the promoter for xylose PXylA, and its repressor XylR, which control the synthesis of T7 RNA polymerase, whose gene sequence is in the same plasmid. The plasmid for synthesis of recombinant proteins, pPT7 (MoBiTec), derives from *B. cereus* and leads to a replication origin of *B. megaterium* and resistance to ampicillin and chloramphenicol, and a replication origin for *E. coli* and the promoter T7 controlled by T7 RNA polymerase.

When the protein of interest is to be synthesised, xylose is added to the cells, and activates its promoter by detaching the repressor. The promoter, freed, then allows the polymerase of the bacterium to transcribe the gene for synthesis of the T7 RNA polymerase enzyme which, moving onto the T7 promoter of the other plasmid, transcribes its gene of interest, namely the genes required for HA synthesis. The system is highly efficient, because a single polymerase is dedicated to the transcription of the gene of interest, and the multiple copies of the two plasmids ensure that the transcript levels are extremely high.

A further object of the present invention are plasmid vectors, containing the two genes hasA and tuaD or the four genes hasA, tuaD, gtaB and pgi (corresponding to hasE), under the control of T7 promoter of RNA polymerase of bacteriophage T7, which are suitable to allow the production in *B. megaterium* and/or in *E. coli*, preferably in *B. megaterium*, of hyaluronic acid in high yield, according to the methodology described above. Preferably, the sequences coding for the hyaluronan synthase enzyme, UDP-glucose dehydrogenase, UDP-glucose pyrophosphorylase and glucose 6 phosphate isomerase include an upstream Shine-Dalgarno sequence. These vectors can also be constructed so as contain any other gene relating to the biosynthesis of hyaluronic acid.

Unlike those available to date, the starting plasmid is small, which allows engineering of the entire hyaluronic acid biosynthesis pathway (i.e. the four genes hasA, tuaD, gtaB and pgi) in a single plasmid, which is herein referred to as pPT7hasAtuaDgtaBpgi, making the present invention economically advantageous and successfully applicable on an industrial scale. In a preferred embodiment of the present invention the plasmid vector is pPT7hasAtuaD (SEQ ID NO:1) or pPT7hasAtuaDgtaBpgi (SEQ ID NO:2).

The present invention also relates to a method and relative system for the production/construction of bacterial strains, transformed with plasmid containing the entire hyaluronic acid biosynthesis pathway, with the 2 genes or 4 genes, and the selection of stable, viable, replicating and HA-secreting bacterial strains with high yield.

Said method of construction of engineered strain with the 2 genes or 4 genes plasmid vector for the HA synthesis comprises the following steps:
Cloning of the tuaD gene (UDP-glucose dehydrogenase) from *Bacillus Subtilis*,
Cloning of the hasA gene (hyaluronan synthase) from *Streptococcus zooepidemicus*,
Construction of the plasmid pGEM4hasA,
Construction of a plasmid with the tuaD gene following hasA,
Cloning of the hasA-tuaD gene in the plasmid for *B. megaterium* pPT7:pPT7hasAtuaD;
the process for the construction of the 4 genes route proceeds with the following steps:
Cloning of the gtaB gene: construction of the plasmid pGEM4hasA-gtaB,
Cloning of the pgi gene from *Bacillus Subtilis*, Construction of plasmid pPT7hasAtuaDgtaBpgi, which is referred to as pT7hyal, Transformation of plasmids pPT7hasAtuaD and pPT7hasAtuaDgtaBpgi into *Bacillus megaterium* or *E. coli*, preferably in *Bacillus megaterium*, Selection of hyaluronic acid-secreting cells by xylose gradient for *Bacillus megaterium* or IPTG gradient for *E. coli*, Selection of stable, viable, replicant and secreting high amounts of HA cells.

A further object of the invention is therefore a system for the selection of transfected, secreting, viable cells: the IPTG gradient allows the selection of transfected, viable cells, capable of replication and above all, secreting HA with high yields.

The present invention will be now disclosed by way of example but not of limitation, according to preferred embodiments with particular reference to the attached figures, wherein.

Figure 3:
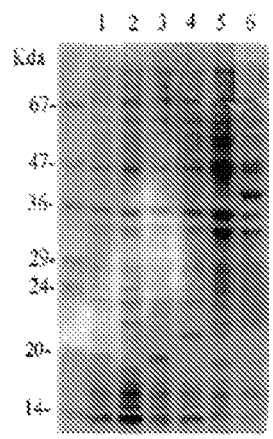
Figure 4:
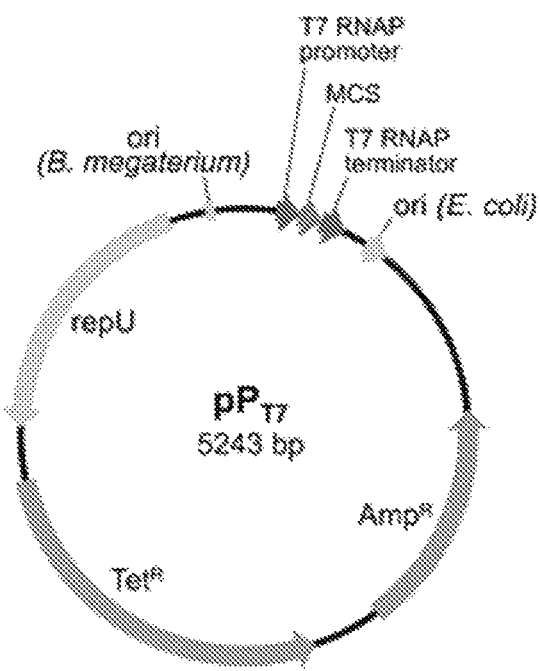
Figure 5:
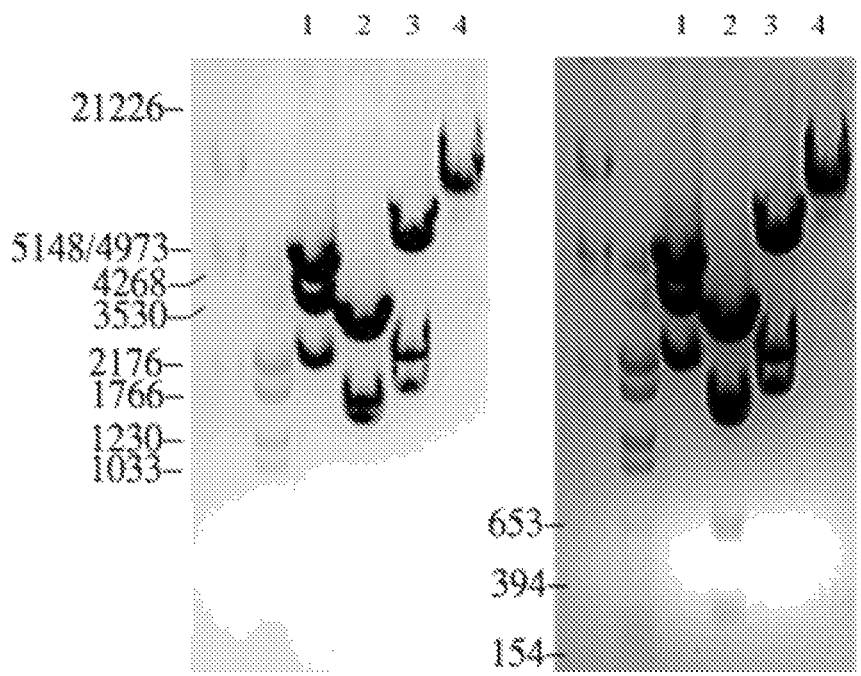
Figure 6:
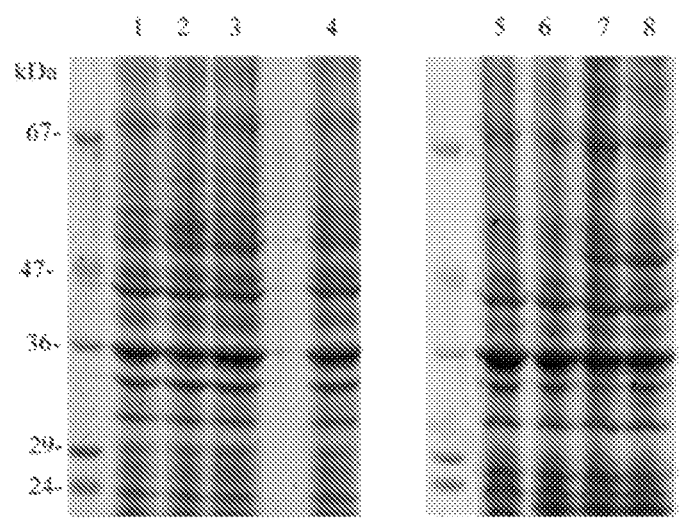
Figure 7:
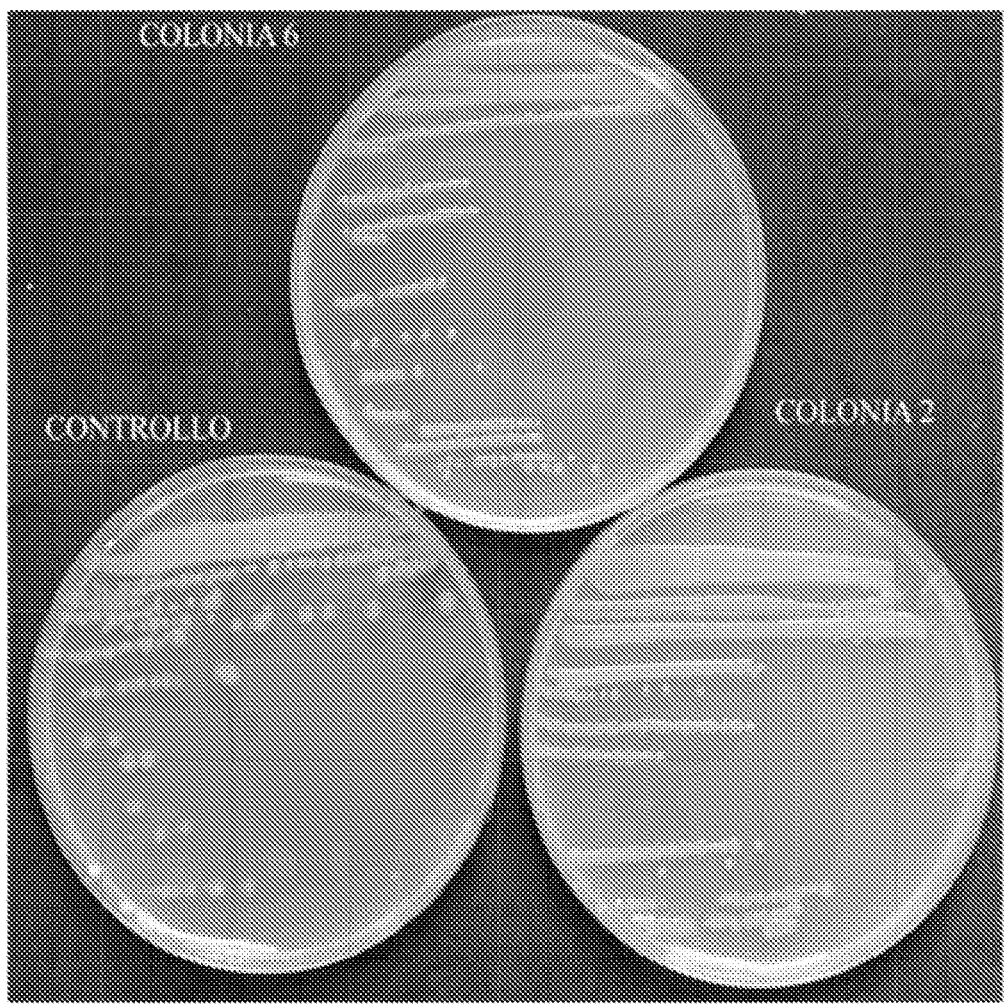
Figure 8:
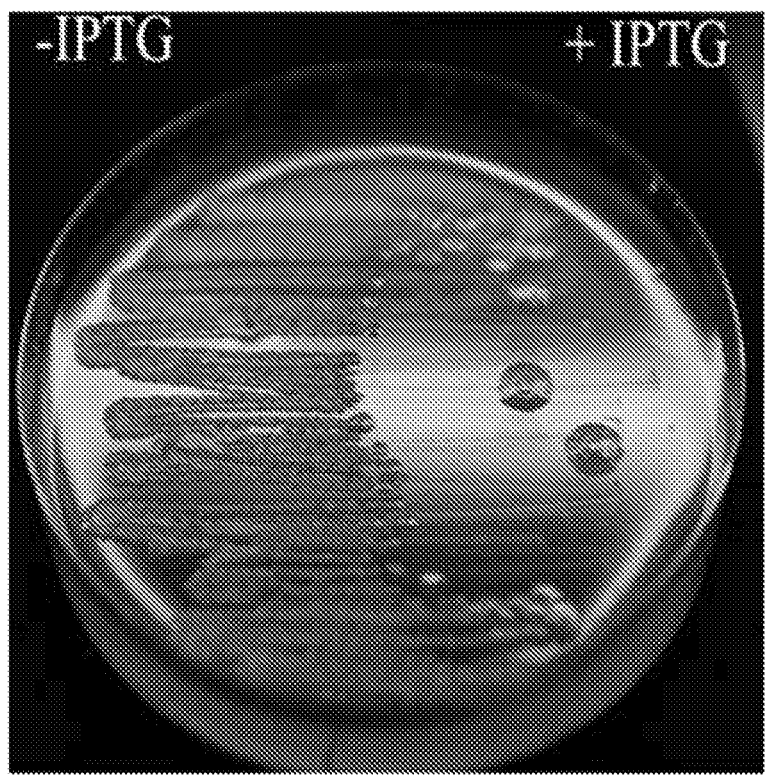
Figure 9:
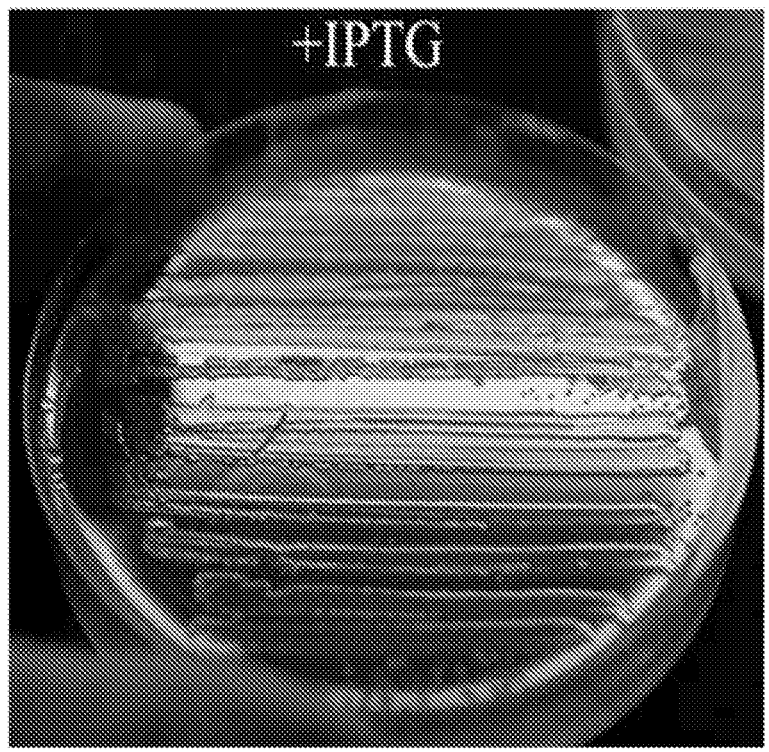
Figure 10:
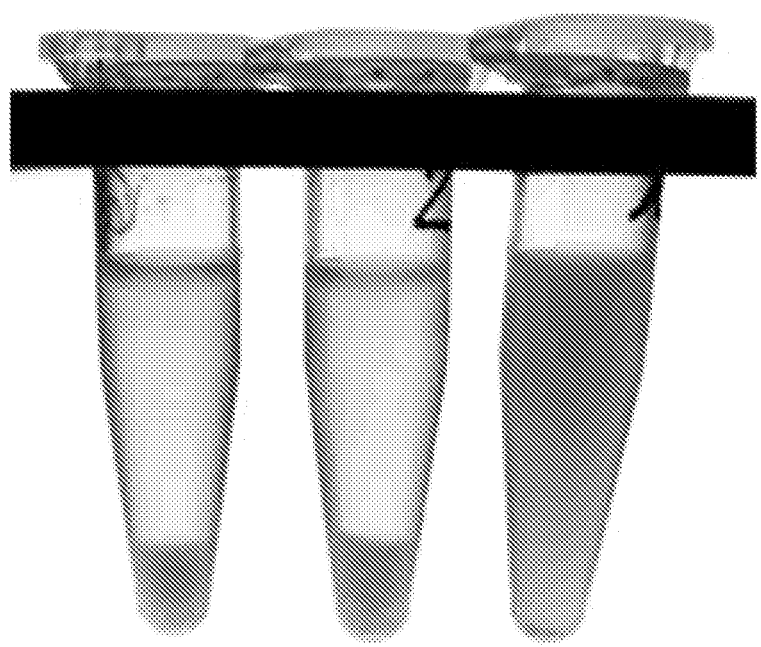

FIG. 3 shows the analysis in gel electrophoresis of the constitutive expression of hyaluronan synthase (Strept) in *E. coli*; the encoded protein designated SeHAS is 417 amino acids long (calculated molecular weight 47,778; calculated PI 9.1) and is the smallest member of the HAS family identified thus far; the enzyme migrates anomalously fast in SDS polyacrylamide gel electrophoresis (about 42000 Da);

FIG. 4 shows the plasmid map pPT7 comprising the promoter and the terminator of T7 RNA polymerase of bacteriophage T7; the replication origin of Coli and Megaterium; ampicillin resistance gene; tetracycline resistance gene;

FIG. 5 shows the restriction map of plasmid PT7hyal;

FIG. 6 shows the analysis by SDS-page of cell lysates of *E. coli* BL21 DE3 to verify the presence of proteins that lead to the synthesis of hyaluronic acid;

FIG. 7 shows the comparison of the production of HA in plate between colonies of *E. coli* BL21 DE3 transformed with the plasmid pPT7 (colony control), pPT7hasAtuaD (colony 6) and pPT7hasAtuaDgtaBpgi (pT7Hyal—Colony 2) after 24 hours of growth at 37° C., in the presence of IPTG;

FIG. 8 shows the results of plating assays for the selection of cells able to express high levels of hyaluronic acid in the presence or absence of IPTG;

FIG. 9 shows the results of plating assays in the presence of IPTG to test the degree of survival of cells capable of producing HA;

FIG. 10 shows the carbazole analysis of the precipitates of HA in the test tube.

The following examples describe the various steps required for the embodiment of the invention, by way of example but not of limitation.

EXAMPLE 1

Cloning of the tuaD Gene (UDP-Glucose Dehydrogenase) from *Bacillus subtilis*

The sequence of the tuaD gene, which is 9300 bp long in *B. subtilis*, is present in the databases under the access number AF015609 in the system which codes for the teichuronic acid operon and comprises eight genes, tuaABCDEFGH. In the present case the gene of interest tuaD falls between bases 3582-4984 bp. Software analysis for restriction enzymes indicates that the restriction sites ClaI, EcoRI, PstI, FHindIII and SphI are present, and therefore cannot be used for cloning. The start codon is not a methionine but a valine; in the present invention, it was replaced with the codon for methionine, which is much more efficient in the transduction of the protein. Two oligonucleotide primers with the following sequence were used to recover this sequence:

```
                                              (SEQ ID NO: 3)
     5' atgaaaaaatagctgtcattggaacag 3'
     and (SEQ ID NO: 4)
     5' ttataaattgtcgttcccaagtct 3'.
```

The genomic DNA from *B. subtilis* strain 168 (ACTT 23857D-5) was obtained with the Qiagen extraction kit. With 32 cycles of PCR, using DNA from *B. subtilis* as template and the two said oligonucleotides, an amplificate of the expected molecular weight was obtained. The amplificate obtained was tested for the presence of restriction enzyme EcoRI. After cutting with this enzyme in 1% agarose gel, two bands of DNA weighing 470 bp and 920 bp were present, which correspond to those expected. To clone the tuaD gene in an expression vector, two other oligonucleotides with the following sequence were synthesised:

```
                                              (SEQ ID NO: 5)
     5' gctggatccatgaaaaaatagctgtcattgg 3'
     and (SEQ ID NO: 6)
     5' ctcgctagcttataaattgacgcttcccaag 3'
``` in order to insert said sequence between the restriction sites BamHI and NheI in the expression vector, plasmid pRSET B (INVITROGEN).

A Shine-Dalgarno (SD) sequence needs to be introduced into gene tuaD upstream of the 5' end of the gene to allow efficient recognition by the bacterial RNA polymerase. For this purpose the DNA was amplified with the following oligonucleotide primers:

```
                                              (SEQ ID NO: 7)
     5' cgacatatgaaaaaatagctgtcattgg 3'
     and (SEQ ID NO: 8)
     5' ctcgctagcttataaattgacgcttcccaag 3' .
```

Two restriction sites NdeI and NheI are present in said primers at 5', which allow their cloning in vector pRSET B between the same sites. A sequence SD, consequently present upstream of restriction site NdeI of plasmid pRSET B, is particularly efficient and necessary for the RNA polymerase in order to synthesise the protein. Restriction site XbaI, which will be required for the subsequent clonings, is also present even before said sequence. The vector created, pRSET B, was therefore called pRSEtuaD.

Thus in this plasmid, the sequence coding for tuaD falls between restriction sites NdeI and NheI; restriction site XbaI, which is necessary for the subsequent cloning, is present before and upstream of said plasmid, and other restriction sites, including BamHI--BglII--XhoI, are present behind the tuaD gene.

The diagram below summarises the sites of interest present in plasmid pRSEtuaD

XbaI--NdeI---------------tuaD-----------------NheI--BamHI--BglII--XhoI

Figure 1:
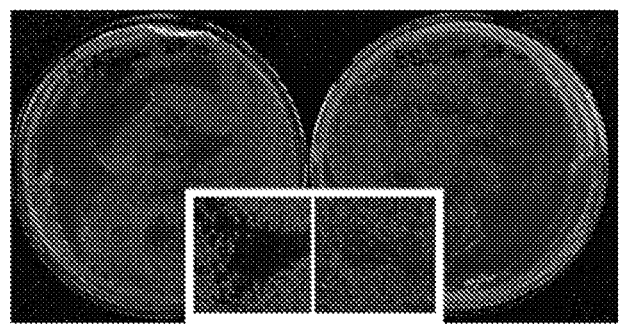
FIG. 1 shows a comparison in plates between the growth of cells *E. coli* TOP10, incorporating plasmid pHT01 (control) and cells *E. coli* TOP10, incorporating pBS5 (hasA+tuaD)

The plasmid described is an expression vector functioning not only in *B. megaterium* but also in *E. coli*, because the gene is under the control of T7 promoter of bacteriophage T7; if it is transformed into bacterial cells BL21 DE3, which are able to transcribe T7 RNA polymerase, it therefore enables them to express the tuaD gene. After induction with 1 mM of IPTG the cells in *E. coli* are able to produce the protein of the expected molecular weight, but not hyaluronic acid. The construction is particularly efficient because the level of expression is very high. The sizes of the colonies which carry plasmid pRSEtuaD are tiny compared with the control cells (FIG. 1), which demonstrates the toxicity of the tuaD gene. This cloning is difficult precisely because it is apparently difficult for the colonies to grow; the particularly high level of enzyme UDP-glucose dehydrogenase probably drains the cell glucose because it is required for the formation of the hyaluronic acid precursor. The cells in which the synthesis of tuaD is induced with IPTG are therefore no longer able to survive for a long time, so the gene product is toxic.

Figure 2:
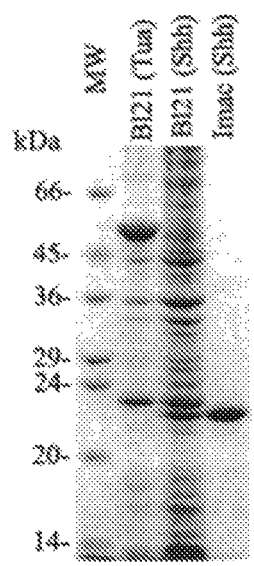
FIG. 2 shows the gel analysis of the expression of gene tuaD in *E. coli* BL21 DE3.

In conclusion, the tuaD gene was isolated and cloned in a plasmid, and the sequence proved correct. The gene expressed in *E. coli* is able to produce a protein of the expected molecular weight (54 kDa, FIG. 2), which is toxic to the cell. However, these cells are unable to produce significant quantities of hyaluronic acid, as hyaluronan synthase (hasA) is lacking.

EXAMPLE 2

Cloning of the hasA (Hyaluronan Synthase) Gene from *Streptococcus zooepidemicus*

The gene sequence for hyaluronan synthase is present in the databases under the access number AY173078, and is 3552 bp long; the sequence coding for the protein is between bases 1 and 1254. The restriction sites HindIII and StuI are present in this sequence, and therefore cannot be used for cloning, but can be used to verify the cloning. Two oligonucleotides for use with PCR were designed and synthesised to recover the coding sequence:

```
                                          (SEQ ID NO: 9)
5' atgagaacattaaaaaacctcataac 3'
and
                                          (SEQ ID NO: 10)
5' taataattttttacgtgttcccag 3'
```

The genomic DNA from the bacterium *Streptococcus zooepidemicus* was recovered with the Qiagen extraction kit. The 1254 bp coding sequence was recovered with PCR. The expected amplificate of the correct dimensions was controlled with restriction enzyme HindIII, and gave rise to two bands of approx. 100 bp and 1150 bp which correspond to the expected cut.

EXAMPLE 3

Construction of the Plasmid pGEM4hasA

Two other oligonucleotides with the following sequence were created to clone the hasA sequence in plasmid pGEM4Z:

```
                                          (SEQ ID NO: 11)
5' ggaggatccatgagaacattaaaaaacctcat 3'
and
                                          (SEQ ID NO: 12)
5' cagtctagattataataattttttacgtgtcc 3'
```

The BamHI restriction site was created in the first oligonucleotide close to 5', and the XbaI restriction site was created in the second oligonucleotide, again at 5'. The amplificate obtained through these two oligonucleotides was cloned between restriction sites BamHI and XbaI in plasmid pGEM4Z (PROMEGA) between the same sites to give plasmid pGEM4hasA.

The DNA sequence between said two restriction sites was analysed with an ABI 7000 sequencer, proved correct, and is identical to the one published.

HindIII-BamHI----------------hasA---------------XbaI-SalI

The plasmid was checked for expression of the recombinant protein in *E. coli* and presented a molecular weight of approx. 42 kDa, which agrees with the weight reported for the protein in the literature, although it has a theoretical molecular weight of 47.778 kDa (FIG. 3).

The cloning of hasA from *streptococcus* was therefore also demonstrated in terms of protein expression. The plasmid is unable to produce significant quantities of hyaluronic acid because it lacks the tuaD gene.

EXAMPLE 4

Construction of a Plasmid with the tuaD Gene Following hasA

With this construction, the hasA gene is placed in tandem with the tuaD gene. For this purpose, plasmid pGEM4hasA, which already contains the hasA gene, is used as vector. The plasmid was cut with XhaI and SalI, and the tuaD gene sequence from plasmid pRSEtuaD was cut with XhaI and XhoI and cloned in the same sites (Xho I and SalI are compatible)

pGEM4hasA
HindIII-BamHI---------------hasA---------------XbaI-SalI
pRSE tuaD
XbaI--NdeI-----------------tuaD-----------------NheI--BamHI--BglI--XhoI
the following final sequence being obtained:
HindIII-BamHI---------hasA----------XbaI--NdeI---------tuaD-----------NheI--BamHI--BglII--XhoI

EXAMPLE 5

Cloning of the hasA-tuaD Gene in the Plasmid pPT7 for *B. megaterium*

This plasmid pPT7 (MoBiTec) contains two origins of replication, one for *E. coli* and one for *B. megaterium*, and can therefore be propagated in both bacteria. It also contains resistance to the antibiotics ampicillin and tetracycline, which can be used for *E. coli* and *B. megaterium* respectively, and the recognition sequence for T7 RNA polymerase, namely the promoter dependent on T7 RNA polymerase of bacteriophage T7 followed by its terminator.

The plasmid contains restriction site BsrGI with the sequence tgtaca a few bases after the Shine-Dalgarno sequence, and a site BamHI (ggatcc) after the initial methionine. Two oligonucleotides were synthesised for the cloning so as to create the following two restriction sites at the end:

```
                                                           (SEQ ID NO: 13)
5' GCTTGTACATGAGAACATTAAAAAACCTCA 3'

(SEQ ID NO: 14)
5' AGGGATCCTTATAAATTGACGCTTCCCAAG 3'
``` i.e. BsrGI and BamHI upstream and downstream of genes hasA and tuaD respectively. The 2698 bp amplificate obtained was cut with the restriction enzymes BsrGI and BamHI and cloned in the same restriction sites as plasmid pPT7 to obtain plasmid pPT7hasAtuaD (FIG. 4).

The complete sequence of this plasmid, called pPT7hasAtuaD, was analysed, and is set out below:

```
                                                            (SEQ ID NO: 1)
   0 CTTTTTAGGTTCTAAATCGTGTTTTTCTTGGAATTGTGCTGTTTTATCCTTTACCTTGTC

60 TACAAACCCCTTAAAAACGTTTTTAAAGGCTTTTAAGCCGTCTGTACGTTCCTTAAGGCG

120 AAATTAATACGACTCACTATAGGGAGACCACAACGGTTTCCCGAATATTAATTAACCAAG

Bsp1407I
 180 GAGGTGAAATGTACAATGAGAACATTAAAAAACCTCATAACTGTTGTGGCCTTTAGTATT
   1             M   R   T   L   K   N   L   I   T   V   V   A   F   S   I

HindIII
 240 TTTTGGGTACTGTTGATTTACGTCAATGTTTATCTCTTTGGTGCTAAAGGAAGCTTGTCA
   1 F   W   V   L   L   I   Y   V   N   V   Y   L   F   G   A   K   G   S   L   S 300 ATTTATGGCTTTTTGCTGATAGCTTACCTATTAGTCAAATGTCCTTATCCTTTTTTTAC
   1 I   Y   G   F   L   L   I   A   Y   L   L   V   K   M   S   L   S   F   F   Y 360 AAGCCATTTAAGGGAAGGGCTGGGCAATATAAGGTTGCAGCCTTATTCCCTCTTATTAAC
   1 K   P   F   K   G   R   A   G   Q   Y   K   V   A   A   I   I   P   S   Y   N 420 GAAGATGCTGAGTCATTGCTAGAGACCTTAAAAAGTGTTCAGCAGCAAACCTATCCCCTA
   1 E   D   A   E   S   L   L   E   T   L   K   S   V   Q   Q   Q   T   Y   P   L 480 GCAGAAATTTATGTTGTTGACGATGGAAGTGCTGATGAGACAGGTATTAAGCGCATTGAA
   1 A   E   I   Y   V   V   D   D   G   S   A   D   E   T   G   I   K   R   I   E 540 GACTATGTGCGTGACACTGGTGACCTATCAAGCAATGTCATTGTTCACCGGTCAGAAAAA
   1 D   Y   V   R   D   T   G   D   L   S   S   N   V   I   V   H   R   S   E   K 600 AATCAAGGAAAGCGTCATGCACAGGCCTGGGCCTTTGAAAGATCAGACGCTGATGTCTTT
   1 N   Q   G   K   R   H   A   Q   A   W   A   F   E   R   S   D   A   D   V   F 660 TTGACCGTTGACTCAGATACTTATATCTACCCTGATGCTTTAGAGGAGTTGTTAAAAACC
   1 L   T   V   D   S   D   T   Y   I   Y   P   D   A   L   E   E   L   L   K   T 720 TTTAATGACCCAACTGTTTTTGCTGCGACGGGTCACCTTAATGTCAGAAATAGACAAACC
   1 F   N   D   P   T   V   F   A   A   T   G   H   L   N   V   R   N   R   Q   T 780 AATCTCTTAACACGCTTGACAGATATTCGCTATGATAATGCTTTTGGCGTTGAACGAGCT
   1 N   L   L   T   R   L   T   D   I   R   Y   D   N   A   F   G   V   E   R   A 840 GCCCAATCCGTTACAGGTAATATTCTCGTTTGCTCAGGCCCGCTTAGCGTTTACAGACGC
   1 A   Q   S   V   T   G   N   I   L   V   C   S   G   P   L   S   V   Y   R   R 900 GAGGTGGTTGTTCCTAACATAGATAGATACATCAACCAGACCTTCCTGGGTATTCCTGTA
   1 E   V   V   V   P   N   I   D   R   Y   I   N   Q   T   F   L   G   I   P   V 960 AGTATCGGTGATGACAGGTGCTTGACCAACTATGCAACTGATTTAGGAAAGACTGTTTAT
   1 S   I   G   D   D   R   C   L   T   N   Y   A   T   D   L   G   K   T   V   Y 1020 CAATCCACTGCTAAATGTATTACAGATGTTCCTGACAAGATGTCTACTTACTTGAAGCAG
   1 Q   S   T   A   K   C   I   T   D   V   P   D   K   M   S   T   Y   L   K   Q 1080 CAAAACCGCTGGAACAAGTCCTTCTTTAGAGAGTCCATTATTTCTGTTAAGAAAATCATG
   1 Q   N   R   W   N   K   S   F   F   R   E   S   I   I   S   V   K   K   I   M 1140 AACAATCCTTTTGTAGCCCTATGGACCATACTTGAGGTGTCTATGTTTATGATGCTTGTT
   1 N   N   P   F   V   A   L   W   T   I   L   E   V   S   M   F   M   M   L   V 1200 TATTCTGTGGTGGATTTCTTTGTAGGCAATGTCAGAGAATTTGATTGGCTCAGGGTTTTG
   1 Y   S   V   V   D   F   F   V   G   N   V   R   E   F   D   W   L   R   V   L 1260 GCCTTTCTGGTGATTATCTTCATTGTTGCTCTTTGTCGTAATATTCACTATATGCTTAAG
   1 A   F   L   V   I   I   F   I   V   A   L   C   R   N   I   H   Y   M   L   K 1320 CACCCGCTGTCCTTCTTGTTATCTCCGTTTTATGGGGTACTGCTTTGTTTGTCCTACAGC
   1 H   P   L   S   F   L   L   S   P   F   Y   G   V   L   L   C   L   S   Y   S

1380 CCTTGAAATTGTATTCTCTTTTTACTATTAGAAATGCTGACTGGGGAACACGTAAAAAAT
   1 P
```

```
                XbaI                                         NdeI
1440 TATTATAATCTAGAAATAATTTTGTTTAACTTTAAGAAGGAGATATACATATGAAAAAAA
       3 M  K  K  I

1500 TAGCTGTCATTGGAACAGGTTATGTAGGACTCGTATCAGGCACTTGCTTTGCGGAGATCG
       3 A  V  I  G  T  G  Y  V  G  L  V  S  G  T  C  F  A  E  I  G

EcoRV   ClaI
1560 GCAATAAAGTTGTTTGCTGTGATATCGATGAATCAAAAATCAGAAGCCTGAAAAATGGGG
       3 N  K  V  V  C  C  D  I  D  E  S  K  I  R  S  L  K  N  G  V

1620 TAATCCCAATCTATGAACCAGGGCTTGCAGACTTAGTTGAAAAAAATGTGCTGGATCAGC
       3 I  P  I  Y  E  P  G  L  A  D  L  V  E  K  N  V  L  D  Q  R

EcoRV
1680 GCCTGACCTTTACGAACGATATCCCGTCTGCCATTCGGGCCTCAGATATTATTTATATTG
       3 L  T  F  T  N  D  I  P  S  A  I  R  A  S  D  I  I  Y  I  A

1740 CAGTCGGAACGCCTATGTCCAAAACAGGTGAAGCTGATTTAACGTACGTCAAAGCGGCGG
       3 V  G  T  P  M  S  K  T  G  E  A  D  L  T  Y  V  K  A  A  A

1800 CGAAAACAATCGGTGAGCATCTTAACGGCTACAAAGTGATCGTAAATAAAAGCACAGTCC
       3 K  T  I  G  E  H  L  N  G  Y  K  V  I  V  N  K  S  T  V  P

1860 CGGTTGGAACAGGGAAACTGGTGCAATCTATCGTTCAAAAAGCCTCAAAGGGGAGATACT
       3 V  G  T  G  K  L  V  Q  S  I  V  Q  K  A  S  K  G  R  Y  S

EcoRI
1920 CATTTGATGTTGTATCTAACCCTGAATTCCTTCGGGAAGGGTCAGCGATTCATGACACGA
       3 F  D  V  V  S  N  P  E  F  L  R  E  G  S  A  I  H  D  T  M

1980 TGAATATGGAGCGTGCCGTGATTGGTTCAACAAGTCATAAAGCCGCTGCCATCATTGAGG
       3 N  M  E  R  A  V  I  G  S  T  S  H  K  A  A  A  I  I  E  E

2040 AACTTCATCAGCCATTCCATGCTCCTGTCATTAAAACAAACCTAGAAAGTGCAGAAATGA
       3 L  H  Q  P  F  H  A  P  V  I  K  T  N  L  E  S  A  E  M  I

EcoRV
2100 TTAAATACGCCGCGAATGCATTTCTGGCGACAAAGATTTCCTTTATCAACGATATCGCAA
       3 K  Y  A  A  N  A  F  L  A  T  K  I  S  F  I  N  D  I  A  N

2160 ACATTTGTGAGCGAGTCGGCGCAGACGTTTCAAAAGTTGCTGATGGTGTTGGTCTTGACA
       3 I  C  E  R  V  G  A  D  V  S  K  V  A  D  G  V  G  L  D  S

2220 GCCGTATCGGCAGAAAGTTCCTTAAAGCTGGTATTGGATTCGGCGGTTCATGTTTTCCAA
       3 R  I  G  R  K  F  L  K  A  G  I  G  F  G  G  S  C  F  P  K

2280 AGGATACAACCGCGCTGCTTCAAATCGCAAAATCGGCAGGCTATCCATTCAAGCTCATCG
       3 D  T  T  A  L  L  Q  I  A  K  S  A  G  Y  P  F  K  L  I  E

2340 AAGCTGTCATTGAAACGAACGAAAAGCAGCGTGTTCATATTGTAGATAAACTTTTGACTG
       3 A  V  I  E  T  N  E  K  Q  R  V  H  I  V  D  K  L  L  T  V

2400 TTATGGGAAGCGTCAAAGGGAGAACCATTTCAGTCCTGGGATTAGCCTTCAAACCGAATA
       3 M  G  S  V  K  G  R  T  I  S  V  L  G  L  A  F  K  P  N  T

2460 CGAACGATGTGAGATCCGCTCCAGCGCTTGATATTATCCCAATGCTGCAGCAGCTGGGCG
       3 N  D  V  R  S  A  P  A  L  D  I  I  P  M  L  Q  Q  L  G  A

HindIII
2520 CCCATGTAAAAGCATACGATCCGATTGCTATTCCTGAAGCTTCAGCGATCCTTGGCGAAC
       3 H  V  K  A  Y  D  P  I  A  I  P  E  A  S  A  T  L  G  E  Q SphI
2580 AGGTCGAGTATTACACAGATGTGTATGCTGCGATGGAAGACACTGATGCATGCCTGATTT
       3 V  E  Y  Y  T  D  V  Y  A  A  M  E  D  T  D  A  C  L  I  L 2640 TAACGGATTGGCCGGAAGTGAAAGAAATGGAGCTTGTAAAAGTGAAAACCCTCTTAAAAC
       3 T  D  W  P  E  V  K  E  M  E  L  V  K  V  K  T  L  L  K  Q 2700 AGCCAGTCATCATTGACGGCAGAAATTTATTTTCACTTGAAGAGATGCAGGCAGCCGGAT
       3 P  V  I  I  D  G  R  N  L  F  S  L  E  E  M  Q  A  A  G  Y 2760 ACATTTATCACTCTATCGGCCGTCCCGCTGTTCGGGGAACGGAACCCTCTGACAAGTATT
       3 I  Y  H  S  I  G  R  P  A  V  R  G  T  E  P  S  D  K  Y  F BamHI
2820 TTCCGGGCTTGCCGCTTGAAGAATTGGCTAAAGACTTGGGAAGCGTCAATTTATAAGGAT
       3 P  G  L  P  L  E  E  L  A  K  D  L  G  S  V  N  L
```

-continued

```
           SphI
2880 CCGGCCGCATGCCGGCTAATCGCGACCGGTTAACTAGCATAACCCCTTGGGGCCTCTAAA

2940 CGGGTCTTGAGGGGTTTTTTGCTAAAGGAGGAACTATATCCGGTCCAAGAATTGGAGCCA

3000 ATCAATTCTTGCGGAGAACTGTGAATGCGCAAACCAACCCTTGGCAGAACATATCCATCG

3060 CGTCCGCCATCTCCAGCAGCCGCACGCGGCGCATCTCGGGCCGCGTTGCTGGCGTTTTTC

3120 CATAGGCTCCGCCCCCCTGACGAGCATCACAAAAATCGACGCTCAAGTCAGAGGTGGCGA

3180 AACCCGACAGGACTATAAAGATACCAGGCGTTTCCCCCTGGAAGCTCCCTCGTGCGCTCT

3240 CCTGTTCCGACCCTGCCGCTTACCGGATACCTGTCCGCCTTTCTCCCTTCGGGAAGCGTG

3300 GCGCTTTCTCATAGCTCACGCTGTAGGTATCTCAGTTCGGTGTAGGTCGTTCGCTCCAAG

3360 CTGGGCTGTGTGCACGAACCCCCCGTTCAGCCCGACCGCTGCGCCTTATCCGGTAACTAT

3420 CGTCTTGAGTCCAACCCGGTAAGACACGACTTATCGCCACTGGCAGCAGCCACTGGTAAC

3480 AGGATTAGCAGAGCGAGGTATGTAGGCGGTGCTACAGAGTTCTTGAAGTGGTGGCCTAAC

3540 TACGGCTACACTAGAAGGACAGTATTTGGTATCTGCGCTCTGCTGAAGCCAGTTACCTTC

3600 GGAAAAAGAGTTGGTAGCTCTTGATCCGGCAAACAAACCACCGCTGGTAGCGGTGGTTTT

3660 TTTGTTTGCAAGCAGCAGATTACGCGCAGAAAAAAAGGATCTCAAGAAGATCCTTTGATC

3720 TTTTCTACGGGGTCTGACGCTCAGTGGAACGAAAACTCACGTTAAGGGATTTTGGTCATG

3780 AGATTATCAAAAAGGATCTTCACCTAGATCCTTTTAAATTAAAAATGAAGTTTTAAATCA

3840 ATCTAAAGTATATATGAGTAAACTTGGTCTGACAGTTACCAATGCTTAATCAGTGAGGCA

3900 CCTATCTCAGCGATCTGTCTATTTCGTTCATCCATAGTTGCCTGACTCCCCGTCGTGTAG

3960 ATAACTACGATACGGGAGGGCTTACCATCTGGCCCCAGTGCTGCAATGATACCGCGAGAC

4020 CCACGCTCACCGGCTCCAGATTTATCAGCAATAAACCAGCCAGCCGGAAGGGCCGAGCGC

4080 AGAAGTGGTCCTGCAACTTTATCCGCCTCCATCCAGTCTATTAATTGTTGCCGGGAAGCT
           PstI
4140 AGAGTAAGTAGTTCGCCAGTTAATAGTTTGCGCAACGTTGTTGCCATTGCTGCAGGCATC
           Hpy99I
4200 GTGGTGTCACGCTCGTCGTTTGGTATGGCTTCATTCAGCTCCGGTTCCCAACGATCAAGG

4260 CGAGTTACATGATCCCCCATGTTGTGCAAAAAAGCGGTTAGCTCCTTCGGTCCTCCGATC

4320 GTTGTCAGAAGTAAGTTGGCCGCAGTGTTATCACTCATGGTTATGGCAGCACTGCATAAT
                                   ScaI
4380 TCTCTTACTGTCATGCCATCCGTAAGATGCTTTTCTGTGACTGGTGAGTACTCAACCAAG

4440 TCATTCTGAGAATAGTGTATGCGGCGACCGAGTTGCTCTTGCCCGGCGTCAACACGGGAT

4500 AATACCGCGCCACATAGCAGAACTTTAAAAGTGCTCATCATTGGAAAACGTTCTTCGGGG

4560 CGAAAACTCTCAAGGATCTTACCGCTGTTGAGATCCAGTTCGATGTAACCCACTCGTGCA

4620 CCCAACTGATCTTCAGCATCTTTTACTTTCACCAGCGTTTCTGGGTGAGCAAAAACAGGA

4680 AGGCAAAATGCCGCAAAAAAGGGAATAAGGGCGACACGGAAATGTTGAATACTCATACTC

4740 TTCCTTTTTCAATATTATTGAAGCATTTATCAGGGTTATTGTCTCATGAGCGGATACATA

4800 TTTGAATGTATTTAGAAAAATAAACAAATAGGGGTTCCGCGCACATTTCCCCGAAAAGTG

4860 CCACCTGACGTCTAAGAAACCATTATTATCATGACATTAACCTATAAAAATAGGCGTATC
           EcoRI
4920 ACGAGGCCCTTTCGTCTTCAAGAATTCCTGTTATAAAAAAAGGATCAATTTTGAACTCTC

4980 TCCCAAAGTTGATCCCTTAACGATTTAGAAATCCCTTTGAGAATGTTTATATACATTCAA

5040 GGTAACCAGCCAACTAATGACAATGATTCCTGAAAAAAGTAATAACAAATTACTATACAG

5100 ATAAGTTGACTGATCAACTTCCATAGGTAACAACCTTTGATCAAGTAAGGGTATGGATAA
```

-continued

```
5160 TAAACCACCTACAATTGCAATACCTGTTCCCTCTGATAAAAAGCTGGTAAAGTTAAGCAA

5220 ACTCATTCCAGCACCAGCTTCCTGCTGTTTCAAGCTACTTGAAACAATTGTTGATATAAC

5280 TGTTTTGGTGAACGAAAGCCCACCTAAAACAAATACGATTATAATTGTCATGAACCATGA

5340 TGTTGTTTCTAAAAGAAAGGAAGCAGTTAAAAAGCTAACAGAAAGAAATGTAACTCCGAT

5400 GTTTAACACGTATAAAGGACCTCTTCTATCAACAAGTATCCCACCAATGTAGCCGAAAAT

ScaI
5460 AATGACACTCATTGTTCCAGGGAAAATAATTACACTTCCGATTTCGGCAGTACTTAGCTG

5520 GTGAACATCTTTCATCATATAAGGAACCATAGAGACAAACCCTGCTACTGTTCCAAATAT

5580 AATTCCCCCACAAAGAACTCCAATCATAAAAGGTATATTTTTCCCTAATCCGGGATCAAC

5640 AAAAGGATCTGTTACTTTCCTGATATGTTTTACAAATATCAGGAATGACAGCACGCTAAC

5700 GATAAGAAAAGAAATGCTATATGATGTTGTAAACAACATAAAAAATACAATGCCTACAGA

EcoRV
5760 CATTAGTATAATTCCTTTGATATCAAAATGACCTTTTATCCTTACTTCTTTCTTTAATAA

5820 TTTCATAAGAAACGGAACAGTCATAATTGTTATCATAGGAATGAGTAGAAGATAGGACCA

5880 ATGAATATAATGGGCTATCATTCCACCAATCGCTGGACCGACTCCTTCTCCCATGGCTAC

ClaI
5940 TATCGATCCAATAAGACCAAATGCTTTACCCCTATTTTCCTTTGGAATATAGCGCGCAAC

6000 TACAACCATTACGAGTGCTGGAAATGCAGCTGCACCAGCCCCTTGAATAAAACGAGCCAT

6060 AATAAGTAAGGAAAAGAAAGAATGGCCAACAAACCCAATTACCGACCCGAAACAATTTAT

6120 TATAATTCCAAATAGGAGTAACCTTTTGATGCCTAATTGATCAGATAGCTTTCCATATAC

6180 AGCTGTTCCAATGGAAAAGGTTAACATAAAGGCTGTGTTCACCCAGTTTGTACTCGCAGG

6240 TGGTTTATTAAAATCATTTGCAATATCAGGTAATGAGACGTTCAAAACCATTTCATTTAA

6300 TACGCTAAAAAAGATAAAATGCAAAGCCAAATTAAAATTTGGTTGTGTCGTAAATTCGA

6360 TTGTGAATAGGATGTATTCACATTTCACCCTCCAATAATGAGGGCAGACGTAGTTTATAG

6420 GGTTAATGATACGCTTCCCTCTTTTAATTGAACCCTGTTACATTCATTACACTTCATAAT

6480 TAATTCCTCCTAAACTTGATTAAAACATTTTACCACATATAAACTAAGTTTTAAATTCAG

6540 TATTTCATCACTTATACAACAATATGGCCCGTTTGTTGAACTACTCTTTAATAAAATAAT

6600 TTTTCCGTTCCCAATTCCACATTGCAATAATAGAAAATCCATCTTCATCGGCTTTTTCGT

6660 CATCATCTGTATGAATCAAATCGCCTTCTTCTGTGTCATCAAGGTTTAATTTTTTATGTA

6720 TTTCTTTTAACAAACCACCATAGGAGATTAACCTTTTACGGTGTAAACCTTCCTCCAAAT

6780 CAGACAAACGTTTCAAATTCTTTTCTTCATCATCGGTCATAAAATCCGTATCCTTTACAG

6840 GATATTTTGCAGTTTCGTCAATTGCCGATTGTATATCCGATTTATATTTATTTTTCGGTC

6900 GAATCATTTGAACTTTTACATTTGGATCATAGTCTAATTTCATTGCCTTTTTCCAAAATT

6960 GAATCCATTGTTTTTGATTCACGTAGTTTTCTGTATTCTTAAAATAAGTTGGTTCCACAC

7020 ATACCAATACATGCATGTGCTGATTATAAGAATTATCTTTATTATTTATTGTCACTTCCG

7080 TTGCACGCATAAAACCAACAAGATTTTTATTAATTTTTTATATTGCATCATTCGGCGAA

7140 ATCCTTGAGCCATATCTGACAAACTCTTATTTAATTCTTCGCCATCATAAACATTTTTAA

7200 CTGTTAATGTGAGAAACAACCAACGAACTGTTGGCTTTTGTTTAATAACTTCAGCAACAA

7260 CCTTTTGTGACTGAATGCCATGTTTCATTGCTCTCCTCCAGTTGCACATTGGACAAAGCC

7320 TGGATTTACAAAACCACACTCGATACAACTTTCTTTCGCCTGTTTCACGATTTTGTTTAT

7380 ACTCTAATATTTCAGCACAATCTTTTACTCTTTCAGCCTTTTTAAATTCAAGAATATGCA

7440 GAAGTTCAAAGTAATCAACATTAGCGATTTTCTTTTCTCTCCATGGTCTCACTTTTCCAC
```

```
-continued
7500 TTTTTGTCTTGTCCACTAAAACCCTTGATTTTTCATCTGAATAAATGCTACTATTAGGAC

7560 ACATAATATTAAAAGAAACCCCCATCTATTTAGTTATTTGTTTGGTCACTTATAACTTTA

7620 ACAGATGGGGTTTTTCTGTGCAACCAATTTTAAGGGTTTTCAATACTTTAAAACACATAC

7680 ATACCAACACTTCAACGCACCTTTCAGCAACTAAAATAAAAATGACGTTATTTCTATATG

7740 TATCAAGATAAGAAAGAACAAGTTCAAAACCATCAAAAAAAGACACCTTTTCAGGTGCTT

7800 TTTTTATTTTATAAACTCATTCCCTGATCTCGACTTCGTTCTTTTTTTACCTCTCGGTTA

7860 TGAGTTAGTTCAAATTCGTT
```

The plasmid has a molecular weight of 7880 bp and contains the various genes responsible for hyaluronic acid synthesis under the control of strong T7 promoter of bacteriophage T7. The hasA synthase sequence from *Streptococcus equi* falls between bases 196 and 1383, and that of the tuaD gene between bases 1430 and 2873.

EXAMPLE 6

Cloning of the gtaB Gene (UDP-Glc Pyrophosphorylase)

The gtaB gene from *Bacillus Subtilis* was recovered from the bacterial genome as above, and through two oligonucleotides having the following sequence:

```
                                                  (SEQ ID NO: 15)
5' ATGTCTAGAATAATAAGGAAGGTGCCTTTTAAATGAA 3'

(SEQ ID NO: 16)
5' CTCTCGAGCTAGCTTAGATTTCTTCTTTGTTTAGTAAAG 3'
```

The amplified product of 925 bp was cut with XbaI and XhoI and cloned in plasmid pGEM4hasA in the same restriction sites; plasmid pGEMhasA-gtaB is obtained in this way.

EXAMPLE 7

Cloning of the pgi Gene from *Bacillus subtilis* in Plasmid pRSET B

The pgi gene (glucose 6 phosphate isomerase, also called phosphoglucoisomerase pgi, corresponding to hasE from *S. zooepidemicus*) was recovered from the bacterial genome as described above with these two oligonucleotides

```
                                                  (SEQ ID NO: 17)
5' TACATATGACGCATGTACGCTTGACTACTCCAAAAG 3'

(SEQ ID NO: 18)
5' ATGCTAGCTCATTTATAATCTTCCAGACGTTTTTCAAG 3'
``` and PCR, and cloned after cutting with restriction enzymes NdeI and NheI in plasmid pRSETB between the same restriction sites. Plasmid pRSEpgi is obtained in this way. It places the pgi gene under the control of a T7 promoter, and when it is transferred to cells of *E. coli* BL21 DE3 it produces the protein of the expected molecular weight. This plasmid was cut with XhaI and PstI, and the 1340 bp fragment was cloned in plasmid pGEMhasA-gtaB between sites NheI and PstI. Restriction site Xba, like NheI, is lost after cloning. In this way the pgi gene is placed behind the gtaB gene. The plasmid, called pGEM hasA-gtaB-pgi, was cut with XbaI and XhoI, and the fragment which contains the sequences coding for gtaB and pgi was cloned in plasmid pRSEtuaD between the same sites. The plasmid obtained was called pRSEtuaD)-gtaB-pgi.

The latter was cut with XhaI and BamHI and the fragment which contains the sequence coding for tuaD, gtaB and pgi was cloned in plasmid pPT7hasAtuaD between the same sites to obtain plasmid pPT7hasAtuaDgtaBpgi, which we will call pT7hyal.

The sequence of plasmid pT7hyal is shown below

```
                                                                    (SEQ ID NO: 2)
  0 CTTTTTAGGTTCTAAATCGTGTTTTTCTTGGAATTGTGCTGTTTTATCCTTTACCTTGTC

60 TACAAACCCCTTAAAAACGTTTTTAAAGGCTTTTAAGCCGTCTGTACGTTCCTTAAGGCG

120 AAATTAATACGACTCACTATAGGGAGACCACAACGGTTTCCCGAATATTAATTAACCAAG

Bsp1404I
180 GAGGTGAAATGTACAATGAGAACATTAAAAAACCTCATAACTGTTGTGGCCTTTAGTATT
  1               M   R   T   L   K   N   L   I   T   V   V   A   F   S   I

HindIII
240 TTTTGGGTACTGTTGATTTACGTCAATGTTTATCTCTTTGGTGCTAAAGGAAGCTTGTCA
  1 C   W   V   L   L   I   Y   V   N   V   Y   L   F   G   A   K   G   S   L   S 300 ATTTATGGCTTTTTGCTGATAGCTTACCTATTAGTCAAAATGTCCTTATCCTTTTTTTAC
  1 I   Y   G   F   L   L   I   A   Y   L   L   V   K   M   S   L   S   F   F   Y 360 AAGCCATTTAAGGGAAGGGCTGGGCAATATAAGGTTGCAGCCATTATTCCCTCTTATAAC
  1 K   P   F   K   G   R   A   G   Q   Y   K   V   A   A   I   I   P   S   Y   N 420 GAAGATGCTGAGTCATTGCTAGAGACCTTAAAAAGTGTTCAGCAGCAAACCTATCCCCTA
  1 E   D   A   E   S   L   L   E   T   L   K   S   V   Q   Q   Q   T   Y   P   L

480 GCAGAAATTTATGTTGTTGACGATGGAAGTGCTGATGAGACAGGTATTAAGCGCATTGAA
```

-continued

```
   1 A  E  I  Y  V  V  D  D  G  S  A  D  E  T  G  I  K  R  I  E

540 GACTATGTGCGTGACACTGGTGACCTATCAAGCAATGTCATTGTTCACCGGTCAGAAAAA
   1 D  Y  V  R  D  T  G  D  L  S  S  N  V  I  V  H  R  S  E  K

600 AATCAAGGAAAGCGTCATGCACAGGCCTGGGCCTTTGAAAGATCAGACGCTGATGTCTTT
   1 N  Q  G  K  R  H  A  Q  A  W  A  F  E  R  S  D  A  D  V  F

660 TTGACCGTTGACTCAGATACTTATATCTACCCTGATGCTTTAGAGGAGTTGTTAAAAACC
   1 L  T  V  D  S  D  T  Y  I  Y  P  D  A  L  E  E  L  L  K  T

720 TTTAATGACCCAACTGTTTTTGCTGCGACGGGTCACCTTAATGTCAGAAATAGACAAACC
   1 F  N  D  P  T  V  F  A  A  T  G  H  L  N  V  R  N  R  Q  T

780 AATCTCTTAACACGCTTGACAGATATTCGCTATGATAATGCTTTTGGCGTTGAACGAGCT
   1 N  L  L  T  R  L  T  D  I  R  Y  D  N  A  F  G  V  E  R  A

840 GCCCAATCCGTTACAGGTAATATTCTCGTTTGCTCAGGCCCGCTTAGCGTTTACAGACGC
   1 A  Q  S  V  T  G  N  I  L  V  C  S  G  P  L  S  V  Y  R  R

900 GAGGTGGTTGTTCCTAACATAGATAGATACATCAACCAGACCTTCCTGGGTATTCCTGTA
   1 E  V  V  V  P  N  I  D  R  Y  I  N  Q  T  F  L  G  I  P  V

960 AGTATCGGTGATGACAGGTGCTTGACCAACTATGCAACTGATTAGGAAAGACTGTTTAT
   1 S  I  G  D  D  R  C  L  T  N  Y  A  T  D  L  G  K  T  V  Y

1020 CAATCCACTGCTAAATGTATTACAGATGTTCCTGACAAGATGTCTACTTACTTGAAGCAG
   1 Q  S  T  A  K  C  I  T  D  V  P  D  K  M  S  T  Y  L  K  Q

1080 CAAAACCGCTGGAACAAGTCCTTCTTTAGAGAGTCCATTATTTCTGTTAAGAAAATCATG
   1 Q  N  R  W  N  K  S  F  F  R  E  S  I  I  S  V  K  K  I  M

1140 AACAATCCTTTTGTAGCCCTATGGACCATACTTGAGGTGTCTATGTTTATGATGCTTGTT
   1 N  N  P  F  V  A  L  W  T  I  L  E  V  S  M  F  M  M  L  V

1200 TATTCTGTGGTGGATTTCTTTGTAGGCAATGTCAGAGAATTTGATTGGCTCAGGGTTTTG
   1 Y  S  V  V  D  F  F  V  G  N  V  R  E  F  D  W  L  R  V  L

1260 GCCTTTCTGGTGATTATCTTCATTGTTGCTCTTTGTCGTAATATTCACTATATGCTTAAG
   1 A  F  L  V  I  I  F  I  V  A  L  C  R  N  T  H  Y  M  L  K

1320 CACCCGCTGTCCTTCTTGTTATCTCCGTTTTATGGGGTACTGCTTTGTTTGTCCTACAGC
   1 H  P  L  S  F  L  L  S  P  F  Y  G  V  L  L  C  L  S  Y  S

1380 CCTTGAAATTGTATTCTCTTTTTACTATTAGAAATGCTGACTGGGGAACACGTAAAAAAT
   1 P

XbaI                                      NdeI
1440 TATTATAATCTAGAAATAATTTTGTTTAACTTTAAGAAGGAGATATACATATGAAAAAAA
   3                                                        M  K  K  I

1500 TAGCTGTCATTGGAACAGGTTATGTAGGACTCGTATCAGGCACTTGCTTTGCGGAGATCG
   3 A  V  I  G  T  G  Y  V  G  L  V  S  G  T  C  F  A  E  I  G
                             EcoRV

ClaI
1560 GCAATAAAGTTGTTTGCTGTGATATCGATGAATCAAAAATCAGAAGCCTGAAAATGGGG
   3 N  K  V  V  C  C  D  I  D  E  S  K  I  R  S  L  K  N  G  V

1620 TAATCCCAATCTATGAACCAGGGCTTGCAGACTTAGTTGAAAAAAATGTGCTGGATCAGC
   3 I  P  I  Y  E  P  G  L  A  D  L  V  E  K  N  V  L  D  Q  R

EcoRV
1680 GCCTGACCTTTACGAACGATATCCCGTCTGCCATTCGGGCCTCAGATATTATTTATATTG
   3 L  T  F  T  N  D  I  P  S  A  I  R  A  S  D  I  I  Y  I  A

1740 CAGTCGGAACGCCTATGTCCAAAACAGGTGAAGCTGATTTAACGTACGTCAAAGCGGCGG
   3 V  G  T  P  M  S  K  T  G  E  A  D  L  T  Y  V  K  A  A  A

1800 CGAAAACAATCGGTGAGCATCTTAACGGCTACAAAGTGATCGTAAATAAAAGCACAGTCC
   3 K  T  I  G  E  H  L  N  G  Y  K  V  I  V  N  K  S  T  V  P

1860 CGGTTGGAACAGGGAAACTGGTGCAATCTATCGTTCAAAAAGCCTCAAAGGGAGATACT
   3 V  G  T  G  K  L  V  Q  S  I  V  Q  K  A  S  K  G  R  Y  S

1920 CATTTGATGTTGTATCTAACCCTGAATTCCTTCGGGAAGGGTCAGCGATTCATGACACGA
   3 F  D  V  V  S  N  P  E  F  L  R  E  G  S  A  I  H  D  T  M

1980 TGAATATGGAGCGTGCCGTGATTGGTTCAACAAGTCATAAAGCCGCTGCCATCATTGAGG
   3 N  M  E  R  A  V  I  G  S  T  S  H  K  A  A  A  I  I  E  E
```

```
                                                    -continued
2040 AACTTCATCAGCCATTCCATGCTCCTGTCATTAAAACAAACCTAGAAAGTGCAGAAATGA
   3   L  H  Q  P  F  H  A  P  V  I  K  T  N  L  E  S  A  E  M  I EcoRV
2100 TTAAATACGCCGCGAATGCATTTCTGGCGACAAAGATTTCCTTTATCAACGATATCGCAA
   3   K  Y  A  A  N  A  F  L  A  T  K  I  S  F  I  N  D  I  A  N 2160 ACATTTGTGAGCGAGTCGGCGCAGACGTTTCAAAAGTTGCTGATGGTGTTGGTCTTGACA
   3   I  C  E  R  V  G  A  D  V  S  K  V  A  D  G  V  G  L  D  S 2220 GCCGTATCGGCAGAAAGTTCCTTAAAGCTGGTATTGGATTCGGCGGTTCATGTTTTCCAA
   3   R  I  G  R  K  F  L  K  A  G  I  G  F  G  G  S  C  F  P  K 2280 AGGATACAACCGCGCTGCTTCAAATCGCAAAATCGGCAGGCTATCCATTCAAGCTCATCG
   3   D  T  T  A  L  L  Q  I  A  K  S  A  G  Y  P  F  K  L  I  E 2340 AAGCTGTCATTGAAACGAACGAAAAGCAGCGTGTTCATATTGTAGATAAACTTTTGACTG
   3   A  V  I  E  T  N  E  K  Q  R  V  H  I  V  D  K  L  L  T  V 2400 TTATGGGAAGCGTCAAAGGGAGAACCATTTCAGTCCTGGGATTAGCCTTCAAACCGAATA
   3   M  G  S  V  K  G  R  T  I  S  V  L  G  L  A  F  K  P  N  T PstI
2460 CGAACGATGTGAGATCCGCTCCAGCGCTTGATATTATCCCAATGCTGCAGCAGCTGGGCG
   3   N  D  V  R  S  A  P  A  L  D  T  I  P  M  L  Q  Q  L  G  A HindIII
2520 CCCATGTAAAAGCATACGATCCGATTGCTATTCCTGAAGCTTCAGCGATCCTTGGCGAAC
   3   H  V  K  A  Y  D  P  I  A  I  P  E  A  S  A  I  L  G  E  Q SphI
2580 AGGTCGAGTATTACACAGATGTGTATGCTGCGATGGAAGACACTGATGCATGCCTGATTT
   3   V  E  Y  Y  T  D  V  Y  A  A  M  E  D  T  D  A  C  L  I  L 2640 TAACGGATTGGCCGGAAGTGAAAGAAATGGAGCTTGTAAAAGTGAAAACCCTCTTAAAAC
   3   T  D  W  P  E  V  K  E  M  E  L  V  K  V  K  T  L  L  K  Q 2700 AGCCAGTCATCATTGACGGCAGAAATTTATTTTCACTTGAAGAGATGCAGGCAGCCGGAT
   3   P  V  I  I  D  G  R  N  L  F  S  L  E  E  M  Q  A  A  G  Y 2760 ACATTTATCACTCTATCGGCCGTCCCGCTGTTCGGGGAACGGAACCCTCTGACAAGTATT
   3   I  Y  H  S  I  G  R  P  A  V  R  G  T  E  P  S  D  K  Y  F 2820 TTCCGGGCTTGCCGCTTGAAGAATTGGCTAAAGACTTGGGAAGCGTCAATTTATAAGCTA
   3   P  G  L  P  L  E  E  L  A  K  D  L  G  S  V  N  L 2880 GAATAATAAGGAAGGTGCCTTTTAAATGAAAAAGTACGTAAAGCCATAATTCCAGCAGC
   2                           M  K  K  V  R  K  A  I  I  P  A  A 2940 AGGCTTAGGAACACGTTTTCTTCCGGCTACGAAAGCAATGCCGAAAGAAATGCTTCCTAT
   2   G  L  G  T  R  F  L  P  A  T  K  A  M  P  K  E  M  L  P  I 3000 CGTTGATAAACCTACCATTCAATACATAATTGAAGAAGCTGTTGAAGCCGGTATTGAAGA
   2   V  D  K  P  T  I  Q  Y  I  I  E  E  A  V  E  A  G  I  E  D 3060 TATTATTATCGTAACAGGAAAAAGCAAGCGTGCGATTGAGGATCATTTTGATTACTCTCC
   2   I  I  I  V  T  G  K  S  K  R  A  I  E  D  H  F  D  Y  S  P 3120 TGAGCTTGAAAGAAACCTAGAAGAAAAAGGAAAAACTGAGCTGCTTGAAAAAGTGAAAAA
   2   E  L  E  R  N  L  E  E  K  G  K  T  E  L  L  E  K  V  K  K 3180 GGCTTCTAACCTGGCTGACATTCACTATATCCGCCAAAAAGAACCTAAAGGTCTCGGACA
   2   A  S  N  L  A  D  I  H  Y  I  R  Q  K  E  P  K  G  L  G  H 3240 TGCTGTCTGGTGCGCACGCAACTTTATCGGCGATGAGCCGTTTGCGGTACTGCTTGGTGA
   2   A  V  W  C  A  R  N  F  I  G  D  E  P  F  A  V-
       L  L  G  D 3300 CGATATTGTTCAGGCTGAAACTCCAGGGTTGCGCCAATTAATGGATGAATATGAAAAAAC
   2   D  I  V  Q  A  E  T  P  G  L  R  Q  L  M  D  E  Y  E  K  T 3360 ACTTTCTTCTATTATCGGTGTTCAGCAGGTGCCCGAAGAAGAAACACACCGCTACGGCAT
   2   L  S  S  I  I  G  V  Q  Q  V  P  E  E  E  T  H  R  Y  G  I 3420 TATTGACCCGCTGACAAGTGAAGGCCGCCGTTATCAGGTGAAAAACTTCGTTGAAAAACC
   2   I  D  P  L  T  S  E  G  R  R  Y  Q  V  K  N  F  V  E  K  P 3480 GCCTAAAGGCACAGCACCTTCTAATCTTGCCATCTTAGGCCGTTACGTATTCACGCCTGA
   2   P  K  G  T  A  P  S  N  L  A  I  L  G  R  Y  V  F  T  P  E BglII
```

```
                                                                           -continued
3540 GATCTTCATGTATTTAGAAGAGCAGCAGGTTGGCGCCGGCGGAGAAATTCAGCTCACAGA
   2  I  F  M  Y  L  E  E  Q  Q  V  G  A  G  G  E  I  Q  L  T  D 3600 CGCCATTCAAAAGCTGAATGAAATTCAAAGAGTGTTTGCTTACGATTTTGAAGGCAAGCG
   2  A  I  Q  K  L  N  E  I  Q  R  V  F  A  Y  D  F  E  G  K  R 3660 TTATGATGTTGGTGAAAAGCTCGGCTTTATCACAACAACTCTTGAATTTGCGATGCAGGA
   2  Y  D  V  G  E  K  L  G  F  I  T  T  T  L  E  F  A  M  Q  D 3720 TAAAGAGCTTCGCGATCAGCTCGTTCCATTTATGGAAGGTTTACTAAACAAAGAAGAAAT
   2  K  E  L  R  D  Q  L  V  P  F  M  E  G  L  L  N  K  E  E  I NdeI
3780 CTAAGCTAGAAATAATTTTGTTTAACTTTAAGAAGGAGATATACATATGACGCATGTACG
   2                                                       M  T  H  V  R 3840 CTTGACTACTCCAAAAGCGTTGACTTTCTTTCCAACGGAACATGAACTTACATACCTGCG
   2  L  T  T  P  K  A  L  T  F  F  P  T  E  H  E  L  T  Y  L  R 3900 GGACTTTGTAAAAACAGCACACCATAATATCCATGAGAAAACAGGCGCGGGCAGCGATTT
   2  D  F  V  K  T  A  H  H  N  I  H  E  K  T  G  A  G  S  D  F EcoRI
3960 TCTAGGCTGGGTGGACCTCCCTGAACATTATGATAAAGAAGAATTCGCGCGCATCCAAAA
   2  L  G  V  K  T  A  H  H  N  I  H  E  K  T  G  A  G  S  D  F 4020 AAGCGCGGAAAAAATCCAATCTGACTCTGATGTCTTGCTTGTTGTCGGCATCGGCGGTTC
   2  S  A  E  K  I  Q  S  D  S  D  V  L  L  V  V  G  I  G  G  S 4080 TTATCTTGGAGCGCGGGCAGCGATTGAAGCGCTGAATCACGCGTTTTATAACACTTTGCC
   2  Y  L  G  A  R  A  A  I  E  A  L  N  H  A  F  Y  N  T  L  P 4140 AAAAGCCAAACGCGGCAATCCGCAAGTCATTTTTAACTTCTCTATTAATGTGATTTCTAA
   2  K  A  K  R  G  N  P  Q  V  I  F  N  F  S  I  N  V  I  S  K HindIII
4200 ATCAGGTACGACAACTGAACCTGCAATCGCTTTCCGTATTTTCCGCAAGCTTCTTGAAGA
   2  S  G  T  T  T  E  P  A  I  A  F  I  R  F  R  K  L  L  E  E 4260 GAAATACGGTAAAGAAGAAGCGAAAGCGCGGATTTATGCAACAACTGATAAAGAGCGCGG
   2  K  Y  G  K  E  E  A  K  A  R  I  Y  A  T  T  D  K  E  R  G 4320 CGCATTAAAAACGCTTTCTAACGAAGAAGGCTTTGAATCATTCGTAATTCCTGACGATGT
   2  A  L  K  T  L  S  N  E  E  G  F  E  S  F  V  I  P  D  D  V 4380 CGGCGGCCGTTATTCAGTTTTAACAGCTGTAGGTCTCTTGCCGATTGCTGTCAGCGGCGT
   2  G  G  R  Y  S  V  L  T  A  V  G  L  L  P  I  A  V  S  G  V 4440 CAACATTGACGACATGATGAAAGGCGCCCTGGATGCGAGCAAAGATTTTGCAACATCTGA
   2  N  I  D  D  M  M  K  G  A  L  D  A  S  K  D  F  A  T  S  E 4500 ACTGGAAGATAACCCAGCATACCAATATGCGGTTGTTCGCAATGTCCTTTATAATAAGGG
   2  L  E  D  N  P  A  P  Q  P  A  V  V  R  N  V  L  Y  N  K  G 4560 CAAAACAATTGAAATGCTCATCAACTACGAACCGGCGCTTCAATACTTTGCGGAATGGTG
   2  K  T  I  E  M  L  I  N  Y  E  P  A  L  Q  Y  F  A  E  W  W 4620 GAAGCAGCTGTTCGGAGAAAGCGAAGGGAAAGATGAGAAGGGCATTTATCCTTCTTCAGC
   2  K  Q  L  F  G  E  S  E  G  K  D  E  K  G  I  Y  P  S  S  A 4680 GAACTATTCAACAGACCTTCATTCTTTAGGCCAGTATGTACAAGAAGGCCGCAGAGATTT
   2  N  Y  S  T  D  L  H  S  L  G  Q  Y  V  Q  E  G  R  R  D  L 4740 ATTCGAAACGGTCCTGAACGTAGAGAAGCCTAAACATGAACTGACAATTGAGGAAGCGGA
   2  F  E  T  V  L  N  V  E  K  P  K  H  E  L  T  I  E  E  A  D 4800 TAACGATCTTGACGGCTTGAACTATTTAGCCGGTAAAACTGTTGATTTCGTTAACAAAAA
   2  N  D  L  D  G  L  N  Y  L  A  G  K  T  V  D  F  V  N  K  K 4860 AGCATTCCAAGGTACAATGCTTGCCCATACAGACGGAAATGTTCCGAACTTAATCGTTAA
   2  A  F  Q  G  T  M  L  A  H  T  D  G  N  V  P  N  L  I  V  N 4920 CATTCCTGAGCTGAATGCATATACTTTTGGATACCTTGTATATTTCTTCGAAAAAGCCTG
   2  I  P  E  L  N  A  Y  T  F  G  Y  L  V  Y  F  F  E  K  A  C 4980 CGCGATGAGCGGTTACCTCCTTGGCGTCAATCCGTTTGACCAGCCTGGTGTAGAAGCGTA
   2  A  M  S  G  Y  L  L  G  V  N  P  F  D  Q  P  G  V  E  A  Y 5040 TAAAGTCAATATGTTTGCGTTACTCGGCAAACCTGGCTTTGAAGAGAAAAAAGCAGAGCT
   2  K  V  N  M  F  A  L  L  G  K  P  G  F  E  E  K  K  A  E  L
```

-continued

```
                NheI
5100 TGAAAAACGTCTGGAAGATTATAAATGAGCTAGCATGACTGGTGGACAGCAAATGGGTCG
  2   E  K  R  L  E  D  Y  K
                                    BamHI KpnI
        SphI     AgeI
5160 GGATCTGTACGACGATGACGATAAGGATCCGGTACCGGCCGCATGCCGGCTAATCGCGAC
5220 CGGTTAACTAGCATAACCCCTTGGGGCCTCTAAACGGGTCTTGAGGGGTTTTTTGCTAAA
5280 GGAGGAACTATATCCGGTCCAAGAATTGGAGCCAATCAATTCTTGCGGAGAACTGTGAAT
5340 GCGCAAACCAACCCTTGGCAGAACATATCCATCGCGTCCGCCATCTCCAGCAGCCGCACG
5400 CGGCGCATCTCGGGCCGCGTTGCTGGCGTTTTTCCATAGGCTCCGCCCCCTGACGAGCA
5460 TCACAAAAATCGACGCTCAAGTCAGAGGTGGCGAAACCCGACAGGACTATAAAGATACCA
5520 GGCGTTTCCCCCTGGAAGCTCCCTCGTGCGCTCTCCTGTTCCGACCCTGCCGCTTACCGG
5580 ATACCTGTCCGCCTTTCTCCCTTCGGGAAGCGTGGCGCTTTCTCATAGCTCACGCTGTAG
5640 GTATCTCAGTTCGGTGTAGGTCGTTCGCTCCAAGCTGGGCTGTGTGCACGAACCCCCCGT
5700 TCAGCCCGACCGCTGCGCCTTATCCGGTAACTATCGTCTTGAGTCCAACCCGGTAAGACA
5760 CGACTTATCGCCACTGGCAGCAGCCACTGGTAACAGGATTAGCAGAGCGAGGTATGTAGG
5820 CGGTGCTACAGAGTTCTTGAAGTGGTGGCCTAACTACGGCTACACTAGAAGGACAGTATT
5880 TGGTATCTGCGCTCTGCTGAAGCCAGTTACCTTCGGAAAAAGAGTTGGTAGCTCTTGATC
5940 CGGCAAACAAACCACCGCTGGTAGCGGTGGTTTTTTTGTTTGCAAGCAGCAGATTACGCG
6000 CAGAAAAAAAGGATCTCAAGAAGATCCTTTGATCTTTTCTACGGGGTCTGACGCTCAGTG
6060 GAACGAAAACTCACGTTAAGGGATTTTGGTCATGAGATTATCAAAAAGGATCTTCACCTA
6120 GATCCTTTTAAATTAAAAATGAAGTTTTAAATCAATCTAAAGTATATATGAGTAAACTTG
6180 GTCTGACAGTTACCAATGCTTAATCAGTGAGGCACCTATCTCAGCGATCTGTCTATTTCG
6240 TTCATCCATAGTTGCCTGACTCCCCGTCGTGTAGATAACTACGATACGGGAGGGCTTACC
6300 ATCTGGCCCCAGTGCTGCAATGATACCGCGAGACCCACGCTCACCGGCTCCAGATTTATC
6360 AGCAATAAACCAGCCAGCCGGAAGGGCCGAGCGCAGAAGTGGTCCTGCAACTTTATCCGC
6420 CTCCATCCAGTCTATTAATTGTTGCCGGGAAGCTAGAGTAAGTAGTTCGCCAGTTAATAG
        PstI
6480 TTTGCGCAACGTTGTTGCCATTGCTGCAGGCATCGTGGTGTCACGCTCGTCGTTTGGTAT
6540 GGCTTCATTCAGCTCCGGTTCCCAACGATCAAGGCGAGTTACATGATCCCCCATGTTGTG
6600 CAAAAAAGCGGTTAGCTCCTTCGGTCCTCCGATCGTTGTCAGAAGTAAGTTGGCCGCAGT
6660 GTTATCACTCATGGTTATGGCAGCACTGCATAATTCTCTTACTGTCATGCCATCCGTAAG
        ScaI
6720 ATGCTTTTCTGTGACTGGTGAGTACTCAACCAAGTCATTCTGAGAATAGTGTATGCGGCG
6780 ACCGAGTTGCTCTTGCCCGGCGTCAACACGGGATAATACCGCGCCACATAGCAGAACTTT
6840 AAAAGTGCTCATCATTGGAAAACGTTCTTCGGGGCGAAAACTCTCAAGGATCTTACCGCT
6900 GTTGAGATCCAGTTCGATGTAACCCACTCGTGCACCCAACTGATCTTCAGCATCTTTTAC
6960 TTTCACCAGCGTTTCTGGGTGAGCAAAAACAGGAAGGCAAAATGCCGCAAAAAAGGGAAT
7020 AAGGGCGACACGGAAATGTTGAATACTCATACTCTTCCTTTTTCAATATTATTGAAGCAT
7080 TTATCAGGGTTATTGTCTCATGAGCGGATACATATTTGAATGTATTTAGAAAAATAAACA
7140 AATAGGGGTTCCGCGCACATTTCCCCGAAAAGTGCCACCTGACGTCTAAGAAACCATTAT
        EcoRI
7200 TATCATGACATTAACCTATAAAAATAGGCGTATCACGAGGCCCTTTCGTCTTCAAGAATT
7260 CCTGTTATAAAAAAAGGATCAATTTTGAACTCTCTCCCAAAGTTGATCCCTTAACGATTT
```

-continued

```
7320 AGAAATCCCTTTGAGAATGTTTATATACATTCAAGGTAACCAGCCAACTAATGACAATGA

7380 TTCCTGAAAAAGTAATAACAAATTACTATACAGATAAGTTGACTGATCAACTTCCATAG

7440 GTAACAACCTTTGATCAAGTAAGGGTATGGATAATAAACCACCTACAATTGCAATACCTG

7500 TTCCCTCTGATAAAAAGCTGGTAAAGTTAAGCAAACTCATTCCAGCACCAGCTTCCTGCT

7560 GTTTCAAGCTACTTGAAACAATTGTTGATATAACTGTTTTGGTGAACGAAAGCCCACCTA

7620 AAACAAATACGATTATAATTGTCATGAACCATGATGTTGTTTCTAAAAGAAAGGAAGCAG

7680 TTAAAAAGCTAACAGAAAGAAATGTAACTCCGATGTTTAACACGTATAAAGGACCTCTTC

7740 TATCAACAAGTATCCCACCAATGTAGCCGAAAATAATGACACTCATTGTTCCAGGGAAAA
       ScaI
7800 TAATTACACTTCCGATTTCGGCAGTACTTAGCTGGTGAACATCTTTCATCATATAAGGAA

7860 CCATAGAGACAAACCCTGCTACTGTTCCAAATATAATTCCCCCACAAAGAACTCCAATCA

7920 TAAAAGGTATATTTTTCCCTAATCCGGGATCAACAAAAGGATCTGTTACTTTCCTGATAT

7980 GTTTTACAAATATCAGGAATGACAGCACGCTAACGATAAGAAAAGAAATGCTATATGATG
       EcoRV
8040 TTGTAAACAACATAAAAAATACAATGCCTACAGACATTAGTATAATTCCTTTGATATCAA

8100 AATGACCTTTTATCCTTACTTCTTTCTTTAATAATTTCATAAGAAACGGAACAGTGATAA

8160 TTGTTATCATAGGAATGAGTAGAAGATAGGACCAATGAATATAATGGGCTATCATTCCAC

8220 CAATCGCTGGACCGACTCCTTCTCCCATGGCTACTATCGATCCAATAAGACCAAATGCTT

8280 TACCCCTATTTTCCTTTGGAATATAGCGCGCAACTACAACCATTACGAGTGCTGGAAATG

8340 CAGCTGCACCAGCCCCTTGAATAAAACGAGCCATAATAAGTAAGGAAAAGAAAGAATGGC

8400 CAACAAACCCAATTACCGACCCGAAACAATTTATTATAATTCCAAATAGGAGTAACCTTT

8460 TGATGCCTAATTGATCAGATAGCTTTCCATATACAGCTGTTCCAATGGAAAAGGTTAACA

8520 TAAAGGCTGTGTTCACCCAGTTTGTACTCGCAGGTGGTTTATTAAAATCATTTGCAATAT

8580 CAGGTAATGAGACGTTCAAAACCATTTCATTTAATACGCTAAAAAAAGATAAAATGCAAA

8640 GCCAAATTAAAATTTGGTTGTGTCGTAAATTCGATTGTGAATAGGATGTATTCACATTTC

8700 ACCCTCCAATAATGAGGGCAGACGTAGTTTATAGGGTTAATGATACGCTTCCCTCTTTTA

8760 ATTGAACCCTGTTACATTCATTACACTTCATAATTAATTCCTCCTAAACTTGATTAAAAC

8820 ATTTTACCACATATAAACTAAGTTTTAAATTCAGTATTTCATCACTTATACAACAATATG

8880 GCCCGTTTGTTGAACTACTCTTTAATAAAATAATTTTTCCGTTCCCAATTCCACATTGCA

8940 ATAATAGAAAATCCATCTTCATCGGCTTTTTCGTCATCATCTGTATGAATCAAATCGCCT

9000 TCTTCTGTGTCATCAAGGTTTAATTTTTATGTATTTCTTTTAACAAACCACCATAGGAG

9060 ATTAACCTTTTACGGTGTAAACCTTCCTCCAAATCAGACAAACGTTTCAAATTCTTTTCT

9120 TCATCATCGGTCATAAAATCCGTATCCTTTACAGGATATTTTGCAGTTTCGTCAATTGCC

9180 GATTGTATATCCGATTTATATTTATTTTTCGGTCGAATCATTTGAACTTTTACATTTGGA

9240 TCATAGTCTAATTTCATTGCCTTTTTCCAAAATTGAATCCATTGTTTTTGATTCACGTAG

9300 TTTTCTGTATTCTTAAAATAAGTTGGTTCCACACATACCAATACATGCATGTGCTGATTA

9360 TAAGAATTATCTTTATTATTTATTGTCACTTCCGTTGCACGCATAAAACCAACAAGATTT

9420 TTATTAATTTTTTTATATTGCATCATTCGGCGAAATCCTTGAGCCATATCTGACAAACTC

9480 TTATTTAATTCTTCGCCATCATAAACATTTTTAACTGTTAATGTGAGAAACAACCAACGA

9540 ACTGTTGGCTTTTGTTTAATAACTTCAGCAACAACCTTTTGTGACTGAATGCCATGTTTC

9600 ATTGCTCTCCTCCAGTTGCACATTGGACAAAGCCTGGATTTACAAAACCACACTCGATAC

9660 AACTTTCTTTCGCCTGTTTCACGATTTTGTTTATACTCTAATATTTCAGCACAATCTTTT
```

```
-continued
9720  ACTCTTTCAGCCTTTTTAAATTCAAGAATATGCAGAAGTTCAAAGTAATCAACATTAGCG

9780  ATTTTCTTTTCTCTCCATGGTCTCACTTTTCCACTTTTTGTCTTGTCCACTAAAACCCTT

9840  GATTTTTCATCTGAATAAATGCTACTATTAGGACACATAATATTAAAAGAAACCCCCATC

9900  TATTTAGTTATTTGTTTGGTCACTTATAACTTTAACAGATGGGGTTTTCTGTGCAACCA

9960  ATTTTAAGGGTTTTCAATACTTTAAAACACATACATACCAACACTTCAACGCACCTTTCA

10020 GCAACTAAAATAAAAATGACGTTATTTCTATATGTATCAAGATAAGAAAGAACAAGTTCA

10080 AAACCATCAAAAAAAGACACCTTTTCAGGTGCTTTTTTTATTTTATAAACTCATTCCCTG

10140 ATCTCGACTTCGTTCTTTTTTTACCTCTCGGTTATGAGTTAGTTCAAATTCGTT
```

This plasmid has a molecular weight of 10194 bp and contains the various genes responsible for hyaluronic acid synthesis under the control of a strong 17 promoter of bacteriophage T7. The hasA sequence from *Streptococcus equi* is included between bases 196 and 1383, that of the tuaD gene between bases 1430 and 2873, the sequence coding for gtaB between bases 2905 and 3781, and that for gpi between bases 3824 and 5125.

EXAMPLE 8

Restriction Map of Plasmid pT7Hyal

When plasmid pT7hyal is cut with restriction enzymes it gives rise to a restriction map which corresponds to that expected after sequencing. In column 1 of FIG. 5, it is shown that the cutting with enzyme EcoRI gives rise to three bands 4900 bp, 3240 bp and 2020 bp from plasmid; in column 2 it is shown that the cutting with EcoRI and HindIII gives rise to six bands 3290 bp, 2950 bp, 1660 bp, 1400 bp, 610 bp, and 290 bp; in column 3 it is shown that the cutting with HindIII gives rise to three bands 6240 bp, 2240 bp and 1690 bp, and in column 4 it is shown that, the cutting with restriction enzyme XbaI, single site gives rise to a single band (FIG. 5).

EXAMPLE 9

Check on Synthesis of Proteins which Lead to Hyaluronic Acid Synthesis

The two plasmids pPT7hasAtuaD and pPT7hasAtuaDgtaBpgi (pT7Hyal) were transformed into bacterial cells of *E. coli* BL21 DE3. After induction with IPTG, the cells were lysed, and the sample obtained was loaded into an SDS-PAGE to test for the presence of the proteins which lead to hyaluronic acid synthesis (FIG. 6). The preparation in column 2 corresponds to cells which carried plasmid pPT7hasAtuaD: as shown in FIG. 6, compared with the control colonies in column 1, column 2 presents a protein with a molecular weight of 54 kDa which corresponds to tuaD, and a protein with a weight of 42 kDa which corresponds to hasA. The samples in column 7 and 8 which carry plasmid pPT7hasAtuaDgtaBpgi produce, compared with control colonies 5 and 6, a protein with a molecular weight of 54 kDa which corresponds to tuaD, a protein with a molecular weight of 51 kDa which corresponds to pgi, a protein with a weight of 42 kDa which corresponds to hasA, and a protein with a molecular weight of 32 kDa which corresponds to gtaB. In conclusion, both plasmids produce the proteins of the expected molecular weight required for hyaluronic acid synthesis.

EXAMPLE 10

Synthesis of Hyaluronic Acid in *E. Coli* and Selection by IPTG Gradient

Plasmids pPT7 (control colony), pPT7hasAtuaD (colony 6) and pPT7hasAtuaDgtaBpgi (pT7Hyal—colony 2) were transformed into bacterial cells BL21 DE3. After 24 hours' growth at 37° C., the colonies were analysed for the production of hyaluronic acid. In solution, the cells which carry plasmids pPT7hasAtuaD (colony 6) or plasmids pPT7hasAtuaDgtaBpgi (colony 2) grow much more slowly, and after induction with IPTG only produce low levels of hyaluronic acid. The cells were then plated in the presence of IPTG (FIG. 7).

The control colonies that carry plasmid pPT7 (and no hyaluronic acid synthesis gene) grow more easily, and are larger and flatter, than colony 6 and colony 2, in which the bacteria are engaged in producing hyaluronic acid; in fact, colonies 2 and 6 are shinier than the control as they produce hyaluronic acid. To select cells able to express high levels of hyaluronic acid, the cells were plated in the presence or absence of IPTG (FIG. 8). In the presence of IPTG the majority of the colonies die, and only some survive, especially those close to the IPTG gradient formed. These cells were selected and replated in the presence of IPTG to establish their survival rate (FIG. 9): all of them remained alive, maintaining their HA synthesis capacity.

The above statements are demonstrated by the fact that the cells of colonies 6 and 2 were cultured in solution for 48 hours in the presence of IPTG and 1% saccharose. 1 ml of this bacterial culture was centrifuged to obtain the precipitate, and the bacterial precipitate was then lysed in the presence of 0.1% SDS for 10 minutes. After adding 2 volumes of absolute ethyl alcohol, the result was as shown in FIG. 10.

As will be seen, only colonies 6 and 2 give rise to a hyaluronic acid precipitate (which was tested with the carbazole test).

EXAMPLE 11

Transformation of Plasmids pPT7hasAtuaD and pPT7hasAtuaDgtaBpgi into *Bacillus megaterium*

The *B. megaterium* used in the present invention is already pre-transformed with plasmid pT7-RNAP (QM B1551 MoBiTec) (this plasmid is able to replicate in both *E. coli* and *B. megaterium* because it contains two origins of replication which allow its propagation in both bacteria). It also contains resistance to ampicillin and chloramphenicol, which can be used for *E. coli* and *B. megaterium* respectively. The plasmid contains the sequence able to code for T7 RNA polymerase under the control of the inducible promoter for xylose, and also contains the repressor for the xylose promoter; if the cells are maintained in the absence of xylose, they are therefore unable to transcribe T7 RNA polymerase.

For the transformation of this bacterium it was necessary to remove its bacterial wall to obtain the protoplasts to use for the transformation. To remove the bacterial wall, 50 ml of LB medium were introduced into a 300 ml Erlenmeyer flask, and 1 ml of *Bacillus megaterium* grown overnight under aerobic conditions was added. When the cell density at OD578 reached the value of 1, the cells were centrifuged at 4500 rpm for 15 minutes. The cells were then suspended in 5 ml of 17.5 g/L of Antibiotic Medium no. 3, 500 mM saccharose, 20 mM sodium maleinate and 20 mM $MgCl_2$ pH6 (buffer SMMP). 50 ml of lysozyme 1 mg/ml in SMMP buffer were added and the mixture was maintained at 37° C. for 60 minutes, so as to remove the cell wall; the cells were then gently centrifuged at 1300 rpm for 10 minutes. The bacterial cells were then suspended in 5 ml of fresh SMMP buffer without stirring, as the protoplasts are sensitive to physical stress. This washing was repeated once more. After suspension, the protoplasts were ready to be used directly for the transformation or to be frozen at −80° C. in SMMP, which contains 15% glycerol. However, the transformations are much more efficient when the protoplasts are freshly prepared. For the transformation, 500 µl of protoplast suspension were mixed with 1 µg of plasmid DNA pPT7hasAtuaD or pPT7hasAtuaDgtaBpgi; 1.5 ml of PEG-P (40% w/v PEG6000 in 1×SMM) were then added, and the mixture was placed at ambient temperature for 2 minutes. 5 ml of SMMP were added, and the tubes were gently mixed by rotation.

The bacteria were centrifuged gently at 3000 rpm for 10 minutes at ambient temperature. The supernatant was discarded, and the almost invisible sediment contained the bacteria of interest. 500 µl of SMMP was added to the bacteria, which were then incubated for 90 minutes at 37° C. under slow stirring, at a maximum of 10 rpm; 2.5 ml of CR5 top agar were then prepared in sterile tubes in a hot bath at 43° C.

The CR5 top agar was prepared by mixing two components:
 a) 51.5 g of saccharose, 3.25 g of MOPS and 0.33 g of NaOH in 250 ml of $H_2O$ pH7.3, sterilised by filtration
 b) 2.0 g of agar, 0.1 g of casaminoacids, 5 g of yeast extract and 142.5 ml of $H_2O$.

After autoclaving for 20 minutes, the two ingredients, cooled to 50° C., were mixed together.

After growth, 100 µl of the above disclosed cell preparation were added to 2.5 ml of top agar, mixed gently by rotating with both hands, and deposited on a pre-heated plate containing the antibiotic (4.5 µg/ml of chloramphenicol and 10 µg/ml of tetracycline). The mixture was incubated overnight at 37° C.; the colonies resulting larger or smaller, depending on their access to air.

EXAMPLE 12

Expression of Hyaluronic Acid in *B. Megaterium*

The transformed *B. megaterium* cells were cultured in LB medium with tetracycline and chloramphenicol up to an optical density at 578 nm of 0.4 at 37° C. The induction was conducted with the addition of 0.5% of D-xylose (w/v), followed by incubation at 37° C. The optical density of the bacteria was read every 30 minutes until the optical density at 600 nm reached 1.5; at this point the cells reached the steady state. These cells, as in the case of *E. coli*, are unable to produce hyaluronic acid directly after induction.

EXAMPLE 13

System for the Selection of Hyaluronic Acid Secreting Cells

To obtain *B. megaterium* cells able to produce hyaluronic acid, the plate selection system presented for *E. coli* was employed, using xylose as inductor instead of IPTG. The cells which produce high levels of hyaluronic acid in the plate were then selected. Those cells survive, and can be cultured. The supernatant contains the hyaluronic acid produced (its presence is confirmed by carbazole analysis when it is precipitated with two volumes of ethanol).

EXAMPLE 14

Fermentation of Transformed *B. Megaterium* Cells Selected on Gradient

*Bacillus megaterium* cells transformed with two genes pPT7hasAtuaD plasmid or with four genes pPT7hasAtuaDgtaBpgi plasmid, and selected on xylose gradient were cultured in a 20 l fermenter in 5 l of MM++ medium and glucose or saccharose as carbon source.

Xylose was added as inductor after the start of fermentation.

In the following some fermentation processes for the production of HA are illustrated, said processes mainly differing because of:
 the starting source of carbon;
 the added feed (glucose or saccharose);
 the fermentation temperature (the temperature can be established in a range of from 20 to 38° C., preferably of from 25 to 35° C.);
 time of fermentation.
 Culture media used:
 LB broth (Miller), pH 7
 MM++(Minimal Medium Bs), pH 7, containing per liter:
 1 g $(NH_4)_2HPO_4$; 1 g $NH_4NO_3$; 2.5 g $K_2HPO_4$; 2.5 g $KH_2PO_4$; 0.2 g $MgSO_4 7H_2O$; 0.01 g $FeSO_4 7H_2O$; 0.007 g $MnSO_4 7H_2O$.

EXAMPLE 14a

Production of HA Having a Weight Average MW Comprised in the Range of 100-500 KD The bacterial strain *B. Megaterium* (QM B1551), transfected with the plasmid pPT7hasAtuaDgtaBpgi selected on xylose gradient 0.5% w/v, as described in Example 13, was used.

Procedure: a single colony resistant to xylose was inoculated into 5 ml of sterile LB medium containing 5 mg/l of tetracycline and the inductor. The culture was grown at 37° C., under stirring at 200 rpm.

After 8 hours, 50 µl of this culture were inoculated into a flask containing 50 ml of the medium mentioned above (containing the inductor), and it was made to grow under the same conditions described above.

Subsequently, spent further 14-16 hours, 2 ml of this culture were inoculated into a flask containing 500 ml of the medium above, and it was made to grow under the same conditions until reaching a $D.O.^{600\,nm}$ of 0.6-0.8.

500 ml of the culture thus obtained were then inoculated in the fermenter containing MM++ medium, and the fermentation conditions involved maintaining the culture under stirring at 600 rpm, aeration with 20-24 liters of air/min, a temperature of 37° C. (the temperature of fermentation can be established in a range between 25° C. and 38° C.), and a pH of 6.9 to 7.1. The initial source of carbon was 2% saccharose.

After 4 hours of fermentation, a 2% saccharose supply was added. At 24 hours of fermentation, xylose was added to a final concentration of 0.5%; this induction proceeded for 4 hours; at the end, 0% saccharose was added in steps.

At the end of fermentation (130 hours), the bacterial culture was discharged and centrifuged at 7500 rpm at 8° C. for 20 minutes.

The fermentation broth thus obtained, clarified as free of the cellular component, was analyzed to determine the concentration of HA with the carbazole method (Bitter and Muir, 1962, *Anal. Biochem.* 4:330-334).

Results: The analysis resulted in a concentration of HA of 3.5 g/l.

Determination of weight average molecular weight MW:

For its analysis it was used the method of the intrinsic viscosity (as described in Terbojevich et al., *Carbohydr. Res.* 1986, 363-377, incorporated herein by reference).

Results: the analyzed HA sample showed a weight average molecular weight MW in the range of 100-300 KD.

EXAMPLE 14b

Production of HA Having a Weight Average MW Comprised in the Range of $1 \times 10^6$-$2 \times 10^6$ D The bacterial strain *B. Megaterium* (QM B1551), transfected with the two genes plasmid pPT7hasAtuaD and with the four genes plasmid pPT7hasAtuaDgtaBpgi, selected on xylose gradient, as described in Example 13, was used.

Procedure: for each plasmid which was used, a single colony resistant to xylose was processed as indicated in example 14a. The initial source of carbon was saccharose at 2%: in this example the further supply was glucose (further experimental tests showed that it can be substituted with equal or lower amounts of saccharose). The fermentation conditions were the same as those used in example 14a with the only difference of the fermentation temperature: 25° C.

The culture media used for the fermentation were those disclosed according to example 14a.

At the end of the process (ended after 24 hours), the fermentation broth was analyzed to determine the concentration of HA with the carbazole method.

Results: *B. Megaterium* (QM B1551), transfected with the two genes plasmid pPT7hasAtuaD: the analysis resulted in a concentration of HA of 2.5 g/l;

*B. Megaterium* (QM B1551), transfected with the four genes plasmid pPT7hasAtuaDgtaBpgi: the analysis resulted in a concentration of HA of 3.2 g/l;

Determination of weight average molecular weight MW:

For its analysis it was used the method of the intrinsic viscosity as indicated in the previous example 14a.

Results: the analyzed HA sample produced by *B. Megaterium* transfected with the two genes plasmid showed a weight average molecular weight MW in the range of $1.3 \times 10^6$-$1.7 \times 10^6$ D;

the analyzed HA sample produced by *B. Megaterium* transfected with the four genes plasmid showed a weight average molecular weight MW in the range of $1.6 \times 10^6$-$2 \times 10^6$ D.

The system engineered in *B. megaterium* is inducible, so the fermentation process can be continued by stimulating the production of HA to obtain the desired weight average molecular weight MW; fermentation times between 80 and 160 hours result in a medium-low weight average molecular weight MW, comprised in the range between 100-500 KD, fermentation times between 40 and 80 hours result in a weight average molecular weight in the range between 500-1000 KD, fermentation times between 12 and 40 hours result in a weight average molecular weight MW in the range $1 \times 10^6$-$3 \times 10^6$ D.

With the experiments and the results obtained above, the Applicant has demonstrated to have perfected a system of production of HA in *B. megaterium* by plasmid vectors by:
 engineering of 2 genes (or 4 genes) plasmid vectors for the synthesis of enzymes needed for the production of said polysaccharide, whose gene control is placed under the control of strong promoter T7 of bacteriophage T7;
 perfecting a system of selection of these transfected strains for the production of stable, viable, replicating and HA secreting strains;
 creating an inducible system of HA production, thus controllable both in order to obtain high concentrations of HA and for the production of said polysaccharide at different weight average molecular weight MW.

The invention claimed is:

1. A process for the preparation of hyaluronic acid in *Bacillus megaterium*, comprising the following steps:
    (a) culturing transformed bacterial host cells of *Bacillus megaterium*, transformed in a stable way with the T7 RNA polymerase system under conditions suitable for the production of hyaluronic acid in the presence of xylose as an inductor, wherein said transformed bacterial host cells are characterised by being further transformed with:
    (i) at least one episomal plasmid vector comprising a sequence coding for the enzyme hyaluronan synthase and a sequence coding for the enzyme UDP-glucose dehydrogenase in tandem under the control of the strong inducible T7 promoter; or
    (ii) at least one episomal plasmid vector comprising a sequence coding for the enzyme hyaluronate synthase, a sequence coding for the enzyme UDP-glucose dehydrogenase, a sequence coding for the enzyme UDP-glucose pyrophosphorylase and a sequence coding for the enzyme glucose 6 phosphate isomerase, under the control of the strong inducible T7 promoter;
    (b) recovering hyaluronic acid from the culture medium, wherein the transformed bacterial host cells of *Bacillus megaterium* transformed in a stable way with the T7 RNA polymerase system and with plasmid vector (i) or (ii) able to produce hyaluronic acid of step a) are preselected on a xylose gradient; and
    the sequences coding for enzymes UDP-glucose dehydrogenase (tuaD), UDP-glucose pyrophosphorylase (gtaB) and glucose 6 phosphate isomerase (pgi) are obtained from *Bacillus subtilis*; and
    wherein the fermentation time is in the range between 80 and 160 hours and the product HA has a weight average molecular weight in the range 100-500 KDa or the fermentation time is in the range between 40 and 80 hours and the product HA has a weight average molecular weight in the range 500-1000 KDa or the fermentation time is in the range between 12 and 40 hours and the product HA has a weight average molecular weight in the range $1 \times 10^6$-$3 \times 10^6$ D.

2. The process according to claim 1, wherein the xylose inducer is added to a concentration of between 0.1% and 10% w/v.

3. The process of claim 2, in which the xylose inducer is added to a concentration of between 0.5% and 1% w/v.

4. The process according to claim 1, wherein said bacterial host cells of *Bacillus megaterium* transformed with the T7 RNA polymerase system belong to *B. megaterium* strain QM B1551 or DSM319.

5. The process according to claim 1, wherein the sequence coding for the enzyme hyaluronan synthase (hasA) is obtained from a strain of *Streptococcus*.

6. The process according to claim 1, in which the sequences coding for the enzyme UDP-glucose dehydrogenase, hyaluronan synthase, UDP-glucose pyrophosphorylase and glucose 6 phosphate isomerase are operatively linked to an upstream Shine-Dalgarno sequence.

7. The process according to claim 1, wherein said plasmid vector (i) comprises the nucleotide sequence of SEQ ID NO: 1.

8. The process according to claim 1, wherein said plasmid vector (ii) comprises the nucleotide sequence of SEQ ID NO:2.

9. The process according to claim 1, wherein said strong inducible T7 promoter of plasmid vector (i) or (ii) is a strong inducible T7 promoter of bacteriophage T7.

10. A plasmid vector comprising a strong inducible bacteriophage T7 promoter operationally linked to a sequence coding for a hyaluronan synthase enzyme and a sequence coding for a UDP-glucose dehydrogenase enzyme in tandem.

11. The plasmid vector according to claim 10, wherein said sequence coding for the enzyme hyaluronan synthase is a hasA gene from *Streptococcus zooepidemicus*, and said sequence coding for the enzyme UDP-glucose dehydrogenase is a tuaD gene from *Bacillus subtilis*.

12. The plasmid vector according to claim 11, comprising the nucleotide sequence SEQ ID NO: 1.

13. A plasmid vector comprising a strong inducible bacteriophage T7 promoter operationally linked to a sequence coding for a hyaluronate synthase enzyme, a sequence coding for a UDP-glucose dehydrogenase enzyme, a sequence coding for a UDP-glucose pyrophosphorylase enzyme and a sequence coding for a glucose 6 phosphate isomerase enzyme.

14. The plasmid vector according to claim 13, wherein said sequence coding for the enzyme hyaluronan synthase is a hasA gene from *Streptococcus zooepidemicus*, said sequence coding for the enzyme UDP-glucose dehydrogenase is a tuaD gene from *Bacillus subtilis*, said sequence coding for the enzyme UDP-glucose pyrophosphorylase is a gtaB gene from *Bacillus subtilis* and said sequence coding for the enzyme glucose 6 phosphate isomerase is a pgi gene from *Bacillus subtilis*.

15. The plasmid vector according to claim 14, comprising the nucleotide sequence SEQ ID NO:2.

16. The plasmid vector according to claim 13, wherein the sequence coding for the enzyme UDP-glucose dehydrogenase, hyaluronan synthase, UDP-glucose pyrophosphorylase and glucose 6 phosphate isomerase are operatively linked to an upstream Shine-Dalgarno sequence.

17. A recombinant host bacterial cell belonging to the genus *Bacillus megaterium* previously transformed with the T7 RNA polymerase system, comprising at least one plasmid vector according to claim 10.

18. A method for obtaining recombinant host bacterial cells according to claim 17, which are capable of producing high levels of hyaluronic acid, comprising selecting bacterial host cells transformed with a plasmid vector comprising a strong inducible bacteriophage T7 promoter operationally linked to a sequence coding for a hyaluronan synthase enzyme and a sequence coding for a UDP-glucose dehydrogenase enzyme in tandem and transformed with a T7 RNA polymerase system, on a xylose gradient.

* * * * *

SEQUENCE LISTING

```
<160> NUMBER OF SEQ ID NOS: 18

<210> SEQ ID NO 1
<211> LENGTH: 7880
<212> TYPE: DNA
<213> ORGANISM: artificial
<220> FEATURE:
<223> OTHER INFORMATION: Plasmid containing hasA and tuaD gene under the
      control of promoter T7

<400> SEQUENCE: 1 cttttaggt  tctaaatcgt  gtttttcttg  gaattgtgct  gttttatcct  ttaccttgtc       60
tacaaacccc  ttaaaaacgt  ttttaaaggc  ttttaagccg  tctgtacgtt  ccttaaggcg     120
aaattaatac  gactcactat  agggagacca  caacggtttc  ccgaatatta  attaaccaag     180
gaggtgaaat  gtacaatgag  aacattaaaa  aacctcataa  ctgttgtggc  ctttagtatt     240
```

```
tttgggtac tgttgattta cgtcaatgtt tatctctttg gtgctaaagg aagcttgtca      300
atttatggct ttttgctgat agcttaccta ttagtcaaaa tgtccttatc ctttttttac      360
aagccattta agggaagggc tgggcaatat aaggttgcag ccattattcc ctcttataac      420
gaagatgctg agtcattgct agagacctta aaaagtgttc agcagcaaac ctatcccta       480 gcagaaattt atgttgttga cgatggaagt gctgatgaga caggtattaa gcgcattgaa      540
gactatgtgc gtgacactgg tgacctatca agcaatgtca ttgttcaccg gtcagaaaaa      600
aatcaaggaa agcgtcatgc acaggcctgg gcctttgaaa gatcagacgc tgatgtcttt      660
ttgaccgttg actcagatac ttatatctac cctgatgctt tagaggagtt gttaaaaacc      720
tttaatgacc caactgtttt tgctgcgacg ggtcaccta atgtcagaaa tagacaaacc       780
aatctcttaa cacgcttgac agatattcgc tatgataatg cttttggcgt tgaacgagct      840
gcccaatccg ttacaggtaa tattctcgtt tgctcaggcc cgcttagcgt ttacagacgc      900
gaggtggttg ttcctaacat agatagatac atcaaccaga ccttcctggg tattcctgta      960
agtatcggtg atgacaggtg cttgaccaac tatgcaactg atttaggaaa gactgtttat     1020
caatccactg ctaaatgtat tacagatgtt cctgacaaga tgtctactta cttgaagcag     1080
caaaaccgct ggaacaagtc cttctttaga gagtccatta tttctgttaa gaaaatcatg     1140
aacaatcctt ttgtagccct atggaccata cttgaggtgt ctatgtttat gatgcttgtt     1200
tattctgtgg tggatttctt tgtaggcaat gtcagagaat ttgattggct cagggttttg     1260
gcctttctgg tgattatctt cattgttgct ctttgtcgta atattcacta tgcttaag       1320 cacccgctgt ccttcttgtt atctccgttt tatgggtac tgctttgttt gtcctacagc      1380
ccttgaaatt gtattctctt tttactatta gaaatgctga ctggggaaca cgtaaaaaat     1440
tattataatc tagaaataat tttgtttaac tttaagaagg agatatacat atgaaaaaaa     1500
tagctgtcat tggaacaggt tatgtaggac tcgtatcagg cacttgcttt gcggagatcg     1560
gcaataaagt tgtttgctgt gatatcgatg aatcaaaaat cagaagcctg aaaaatgggg     1620
taatcccaat ctatgaacca gggcttgcag acttagttga aaaaaatgtg ctggatcagc     1680
gcctgacctt tacgaacgat atcccgtctg ccattcgggc ctcagatatt atttatattg     1740
cagtcggaac gcctatgtcc aaaacaggtg aagctgattt aacgtacgtc aaagcggcgg     1800
cgaaaacaat cggtgagcat cttaacggct acaaagtgat cgtaaataaa agcacagtcc     1860
cggttggaac agggaaactg gtgcaatcta tcgttcaaaa agcctcaaag gggagatact     1920
catttgatgt tgtatctaac cctgaattcc ttcgggaagg gtcagcgatt catgacacga     1980
tgaatatgga gcgtgccgtg attggttcaa caagtcataa agccgctgcc atcattgagg     2040
aacttcatca gccattccat gctcctgtca ttaaaacaaa cctagaaagt gcagaaatga     2100
ttaaatacgc cgcgaatgca tttctggcga caaagatttc ctttatcaac gatatcgcaa     2160
acatttgtga gcgagtcggc gcagacgttt caaagttgc tgatggtgtt ggtcttgaca      2220
gccgtatcgg cagaaagttc cttaaagctg gtattggatt cggcggttca tgttttccaa     2280
aggatacaac cgcgctgctt caaatcgcaa atcggcagg ctatccattc aagctcatcg      2340
aagctgtcat tgaaacgaac gaaaagcagc gtgttcatat tgtagataaa cttttgactg     2400
ttatgggaag cgtcaaaggg agaaccattt cagtcctggg attagccttc aaaccgaata     2460
cgaacgatgt gagatccgct ccagcgcttg atattatccc aatgctgcag cagctgggcg     2520
cccatgtaaa agcatacgat ccgattgcta ttcctgaagc ttcagcgatc cttggcgaac     2580
aggtcgagta ttacacagat gtgtatgctg cgatggaaga cactgatgca tgcctgattt     2640
```

```
taacggattg gccggaagtg aaagaaatgg agcttgtaaa agtgaaaacc ctcttaaaac     2700
agccagtcat cattgacggc agaaatttat tttcacttga agagatgcag gcagccggat     2760
acatttatca ctctatcggc cgtcccgctg ttcggggaac ggaaccctct gacaagtatt     2820
ttccgggctt gccgcttgaa gaattggcta agacttggg aagcgtcaat ttataaggat      2880
ccggccgcat gccggctaat cgcgaccggt taactagcat aaccccttgg ggcctctaaa     2940
cgggtcttga ggggttttt gctaaaggag gaactatatc cggtccaaga attggagcca     3000
atcaattctt gcggagaact gtgaatgcgc aaaccaaccc ttggcagaac atatccatcg     3060
cgtccgccat ctccagcagc cgcacgcggc gcatctcggg ccgcgttgct ggcgttttc     3120 cataggctcc gccccctga cgagcatcac aaaaatcgac gctcaagtca gaggtggcga     3180
aacccgacag gactataaag ataccaggcg tttccccctg gaagctccct cgtgcgctct     3240
cctgttccga ccctgccgct taccggatac ctgtccgcct ttctcccttc gggaagcgtg     3300
gcgctttctc atagctcacg ctgtaggtat ctcagttcgg tgtaggtcgt tcgctccaag     3360
ctgggctgtg tgcacgaacc ccccgttcag cccgaccgct gcgccttatc cggtaactat     3420
cgtcttgagt ccaacccggt aagacacgac ttatcgccac tggcagcagc cactggtaac     3480
aggattagca gagcgaggta tgtaggcggt gctacagagt tcttgaagtg gtggcctaac     3540
tacggctaca ctagaaggac agtatttggt atctgcgctc tgctgaagcc agttaccttc     3600
ggaaaaagag ttggtagctc ttgatccggc aaacaaacca ccgctggtag cggtggtttt     3660
tttgtttgca agcagcagat tacgcgcaga aaaaaaggat ctcaagaaga tcctttgatc     3720
ttttctacgg ggtctgacgc tcagtggaac gaaaactcac gttaagggat tttggtcatg     3780
agattatcaa aaaggatctt cacctagatc cttttaaatt aaaaatgaag ttttaaatca     3840
atctaaagta tatatgagta aacttggtct gacagttacc aatgcttaat cagtgaggca     3900
cctatctcag cgatctgtct atttcgttca tccatagttg cctgactccc cgtcgtgtag     3960
ataactacga tacgggaggg cttaccatct ggccccagtg ctgcaatgat accgcgagac     4020
ccacgctcac cggctccaga tttatcagca ataaaccagc cagccggaag ggccgagcgc     4080
agaagtggtc ctgcaacttt atccgcctcc atccagtcta ttaattgttg ccgggaagct     4140
agagtaagta gttcgccagt taatagtttg cgcaacgttg ttgccattgc tgcaggcatc     4200
gtggtgtcac gctcgtcgtt tggtatggct tcattcagct ccggttccca acgatcaagg     4260
cgagttacat gatcccccat gttgtgcaaa aaagcggtta gctccttcgg tcctccgatc     4320
gttgtcagaa gtaagttggc cgcagtgtta tcactcatgg ttatggcagc actgcataat     4380
tctcttactg tcatgccatc cgtaagatgc ttttctgtga ctggtgagta ctcaaccaag     4440
tcattctgag aatagtgtat gcggcgaccg agttgctctt gcccggcgtc aacacgggat     4500
aataccgcgc cacatagcag aactttaaaa gtgctcatca ttggaaaacg ttcttcgggg     4560
cgaaaactct caaggatctt accgctgttg agatccagtt cgatgtaacc cactcgtgca     4620
cccaactgat cttcagcatc ttttactttc accagcgttt ctgggtgagc aaaaacagga     4680
aggcaaaatg ccgcaaaaaa gggaataagg gcgacacgga aatgttgaat actcatactc     4740
ttcctttttc aatattattg aagcatttat cagggttatt gtctcatgag cggatacata     4800
tttgaatgta tttagaaaaa taaacaaata ggggttccgc gcacatttcc ccgaaaagtg     4860
ccacctgacg tctaagaaac cattattatc atgacattaa cctataaaaa taggcgtatc     4920
acgaggccct ttcgtcttca agaattcctg ttataaaaaa aggatcaatt ttgaactctc     4980
```

```
tcccaaagtt gatcccttaa cgatttagaa atcccttttga gaatgtttat atacattcaa    5040
ggtaaccagc caactaatga caatgattcc tgaaaaaagt aataacaaat tactatacag    5100
ataagttgac tgatcaactt ccataggtaa caacctttga tcaagtaagg gtatggataa    5160
taaaccacct acaattgcaa tacctgttcc ctctgataaa aagctggtaa agttaagcaa    5220
actcattcca gcaccagctt cctgctgttt caagctactt gaaacaattg ttgatataac    5280
tgttttggtg aacgaaagcc cacctaaaac aaatacgatt ataattgtca tgaaccatga    5340
tgttgtttct aaaagaaagg aagcagttaa aaagctaaca gaaagaaatg taactccgat    5400
gtttaacacg tataaaggac ctcttctatc aacaagtatc ccaccaatgt agccgaaaat    5460
aatgacactc attgttccag ggaaaataat tacacttccg atttcggcag tacttagctg    5520
gtgaacatct ttcatcatat aaggaaccat agagacaaac cctgctactg ttccaaaatat    5580
aattccccca caagaactc caatcataaa aggtatattt ttccctaatc cgggatcaac    5640
aaaaggatct gttactttcc tgatatgttt tacaaatatc aggaatgaca gcacgctaac    5700
gataagaaaa gaaatgctat atgatgttgt aaacaacata aaaaatacaa tgcctacaga    5760
cattagtata attcctttga tatcaaaatg accttttatc cttacttctt tcttttaataa    5820
tttcataaga aacggaacag tgataattgt tatcatagga atgagtagaa gataggacca    5880
atgaatataa tgggctatca ttccaccaat cgctggaccg actccttctc ccatggctac    5940
tatcgatcca ataagaccaa atgctttacc cctattttcc tttggaatat agcgcgcaac    6000
tacaaccatt acgagtgctg gaaatgcagc tgcaccagcc ccttgaataa aacgagccat    6060
aataagtaag gaaaagaaag aatggccaac aaacccaatt accgacccga aacaattttat    6120
tataattcca aataggagta accttttgat gcctaattga tcagatagct ttccatatac    6180
agctgttcca atggaaaagg ttaacataaa ggctgtgttc acccagtttg tactcgcagg    6240
tggtttatta aaatcatttg caatatcagg taatgagacg ttcaaaacca tttcattttaa    6300
tacgctaaaa aaagataaaa tgcaaagcca aattaaaatt tggttgtgtc gtaaattcga    6360
ttgtgaatag gatgtattca catttcaccc tccaataatg agggcagacg tagtttatag    6420
ggttaatgat acgcttccct ctttttaattg aaccctgtta cattcattac acttcataat    6480
taattcctcc taaacttgat taaaacattt taccacatat aaactaagtt ttaaattcag    6540
tatttcatca cttatacaac aatatggccc gtttgttgaa ctactcttta ataaaataat    6600
ttttccgttc ccaattccac attgcaataa tagaaaatcc atcttcatcg gcttttttcgt    6660
catcatctgt atgaatcaaa tcgccttctt ctgtgtcatc aaggtttaat ttttatgta    6720
tttcttttaa caaaccacca taggagatta accttttacg gtgtaaacct tcctccaaat    6780
cagacaaacg tttcaaattc ttttcttcat catcggtcat aaaatccgta tcctttacag    6840
gatattttgc agtttcgtca attgccgatt gtatatccga tttatattta ttttttcggtc    6900
gaatcatttg aacttttaca tttggatcat agtctaattt cattgccttt ttccaaaatt    6960
gaatccattg ttttttgattc acgtagtttt ctgtattctt aaaataagtt ggttccacac    7020
ataccaatac atgcatgtgc tgattataag aattatcttt attatttatt gtcacttccg    7080
ttgcacgcat aaaaccaaca agattttttat taatttttttt atattgcatc attcggcgaa    7140
atccttgagc catatctgac aaactcttat ttaattcttc gccatcataa acatttttaa    7200
ctgttaatgt gagaaacaac caacgaactg ttggcttttg tttaataact tcagcaacaa    7260
cctttttgtga ctgaatgcca tgtttcattg ctctcctcca gttgcacatt ggacaaagcc    7320
tggatttaca aaaccacact cgatacaact ttctttcgcc tgtttcacga ttttgtttat    7380
```

-continued

```
actctaatat tcagcacaa tcttttactc tttcagcctt tttaaattca agaatatgca      7440
gaagttcaaa gtaatcaaca ttagcgattt tcttttctct ccatggtctc acttttccac      7500
tttttgtctt gtccactaaa acccttgatt tttcatctga ataaatgcta ctattaggac      7560
acataatatt aaaagaaacc cccatctatt tagttatttg tttggtcact tataacttta      7620
acagatgggg ttttctgtg caaccaattt taagggtttt caatacttta aaacacatac       7680
ataccaacac ttcaacgcac ctttcagcaa ctaaaataaa aatgacgtta tttctatatg      7740
tatcaagata agaaagaaca agttcaaaac catcaaaaaa agacaccttt tcaggtgctt      7800 ttttatttt ataaactcat tccctgatct cgacttcgtt cttttttac ctctcggtta       7860 tgagttagtt caaattcgtt                                                   7880
```

<210> SEQ ID NO 2
<211> LENGTH: 10194
<212> TYPE: DNA
<213> ORGANISM: artificial
<220> FEATURE:
<223> OTHER INFORMATION: Plasmid containing hasA, tuaD, gtaB, pgi gene
      under the control of T7 promoter

<400> SEQUENCE: 2

```
cttttaggt tctaaatcgt gtttttcttg gaattgtgct gttttatcct ttaccttgtc       60
tacaaacccc ttaaaacgt tttaaaggc ttttaagccg tctgtacgtt ccttaaggcg        120
aaattaatac gactcactat agggagacca caacggtttc ccgaatatta attaaccaag      180
gaggtgaaat gtacaatgag aacattaaaa aacctcataa ctgttgtggc ctttagtatt      240
ttttgggtac tgttgattta cgtcaatgtt tatctctttg gtgctaaagg aagcttgtca      300
atttatggct ttttgctgat agcttaccta ttagtcaaaa tgtccttatc cttttttac      360 aagccattta agggaagggc tgggcaatat aaggttgcag ccattattcc ctcttataac      420
gaagatgctg agtcattgct agagacctta aaaagtgttc agcagcaaac ctatcccta      480 gcagaaattt atgttgttga cgatggaagt gctgatgaga caggtattaa gcgcattgaa      540
gactatgtgc gtgacactgg tgacctatca agcaatgtca ttgttcaccg gtcagaaaaa      600
aatcaaggaa agcgtcatgc acaggcctgg gcctttgaaa gatcagacgc tgatgtcttt      660
ttgaccgttg actcagatac ttatatctac cctgatgctt tagaggagtt gttaaaaacc      720
tttaatgacc caactgtttt tgctgcgacg ggtcaccttta atgtcagaaa tagacaaacc      780
aatctcttaa cacgcttgac agatattcgc tatgataatg cttttggcgt tgaacgagct      840
gcccaatccg ttacaggtaa tattctcgtt tgctcaggcc cgcttagcgt ttacagacgc      900
gaggtggttt tcctaacat agatagatac atcaaccaga ccttcctggg tattcctgta       960
agtatcggtg atgacaggtg cttgaccaac tatgcaactg atttaggaaa gactgtttat      1020
caatccactg ctaaatgtat tacagatgtt cctgacaaga tgtctactta cttgaagcag     1080
caaaaccgct ggaacaagtc cttctttaga gagtccatta tttctgttaa gaaaatcatg     1140
aacaatcctt ttgtagccct atggaccata cttgaggtgt ctatgttat gatgcttgtt     1200 tattctgtgg tggatttctt tgtaggcaat gtcagagaat tgattggct cagggttttg     1260 gcctttctgg tgattatctt cattgttgct ctttgtcgta atattcacta tatgcttaag     1320 caccccgctgt ccttcttgtt atctccgttt tatgggtac tgctttgttt gtcctacagc     1380
ccttgaaatt gtattctctt tttactatta gaaatgctga ctggggaaca cgtaaaaaat     1440
tattataatc tagaaataat tttgttaac tttaagaagg agatatacat atgaaaaaa      1500
```

```
tagctgtcat tggaacaggt tatgtaggac tcgtatcagg cacttgcttt gcggagatcg    1560
gcaataaagt tgtttgctgt gatatcgatg aatcaaaaat cagaagcctg aaaaatgggg    1620
taatcccaat ctatgaacca gggcttgcag acttagttga aaaaaatgtg ctggatcagc    1680
gcctgacctt tacgaacgat atcccgtctg ccattcgggc ctcagatatt atttatattg    1740
cagtcggaac gcctatgtcc aaaacaggtg aagctgattt aacgtacgtc aaagcggcgg    1800
cgaaaacaat cggtgagcat cttaacggct acaaagtgat cgtaaataaa agcacagtcc    1860
cggttggaac agggaaactg gtgcaatcta tcgttcaaaa agcctcaaag gggagatact    1920
catttgatgt tgtatctaac cctgaattcc ttcgggaagg gtcagcgatt catgacacga    1980
tgaatatgga gcgtgccgtg attggttcaa caagtcataa agccgctgcc atcattgagg    2040
aacttcatca gccattccat gctcctgtca ttaaaacaaa cctagaaagt gcagaaatga    2100
ttaaatacgc cgcgaatgca tttctggcga caaagatttc ctttatcaac gatatcgcaa    2160
acatttgtga gcgagtcggc gcagacgttt caaaagttgc tgatggtgtt ggtcttgaca    2220
gccgtatcgg cagaaagttc cttaaagctg gtattggatt cggcggttca tgttttccaa    2280
aggatacaac cgcgctgctt caaatcgcaa aatcggcagg ctatccattc aagctcatcg    2340
aagctgtcat tgaaacgaac gaaaagcagc gtgttcatat tgtagataaa cttttgactg    2400
ttatgggaag cgtcaaaggg agaaccattt cagtcctggg attagccttc aaaccgaata    2460
cgaacgatgt gagatccgct ccagcgcttg atattatccc aatgctgcag cagctgggcg    2520
cccatgtaaa agcatacgat ccgattgcta ttcctgaagc ttcagcgatc cttggcgaac    2580
aggtcgagta ttacacagat gtgtatgctg cgatggaaga cactgatgca tgcctgattt    2640
taacggattg gccggaagtg aaagaaatgg agcttgtaaa agtgaaaacc ctcttaaaac    2700
agccagtcat cattgacggc agaaatttat tttcacttga agagatgcag gcagccggat    2760
acatttatca ctctatcggc cgtcccgctg ttcggggaac ggaaccctct gacaagtatt    2820
ttccgggctt gccgcttgaa gaattggcta agacttggg aagcgtcaat ttataagcta    2880
gaataataag gaaggtgcct tttaaatgaa aaaagtacgt aaagccataa ttccagcagc    2940
aggcttagga acacgttttc ttccggctac gaaagcaatg ccgaaagaaa tgcttcctat    3000
cgttgataaa cctaccattc aatacataat tgaagaagct gttgaagccg gtattgaaga    3060
tattattatc gtaacaggaa aaagcaagcg tgcgattgag gatcattttg attactctcc    3120
tgagcttgaa agaaacctag aagaaaagg aaaaactgag ctgcttgaaa agtgaaaaaa    3180
ggcttctaac ctggctgaca ttcactatat ccgccaaaaa gaacctaaag gtctcggaca    3240
tgctgtctgg tgcgcacgca actttatcgg cgatgagccg tttgcggtac tgcttggtga    3300
cgatattgtt caggctgaaa ctccagggtt gcgccaatta atggatgaat atgaaaaaac    3360
actttcttct attatcggtg ttcagcaggt gcccgaagaa gaaacacacc gctacggcat    3420
tattgacccg ctgacaagtg aaggccgccg ttatcaggtg aaaaacttcg ttgaaaaacc    3480
gcctaaaggc acagcacctt ctaatcttgc catcttaggc cgttacgtat tcacgcctga    3540
gatcttcatg tatttagaag agcagcaggt tggcgccggc ggagaaattc agctcacaga    3600
cgccattcaa aagctgaatg aaattcaaag agtgtttgct tacgattttg aaggcaagcg    3660
ttatgatgtt ggtgaaaagc tcggctttat cacaacaact cttgaatttg cgatgcagga    3720
taaagagctt cgcgatcagc tcgttccatt tatggaaggt ttactaaaca aagaagaaat    3780
ctaagctaga aataatttg tttaactta agaaggagat atacatatga cgcatgtacg    3840
```

```
cttgactact ccaaaagcgt tgactttctt tccaacggaa catgaactta catacctgcg    3900
ggactttgta aaacagcac accataatat ccatgagaaa acaggcgcgg gcagcgattt    3960
tctaggctgg gtggacctcc ctgaacatta tgataaagaa gaattcgcgc gcatccaaaa    4020
aagcgcggaa aaaatccaat ctgactctga tgtcttgctt gttgtcggca tcggcggttc    4080
ttatcttgga gcgcgggcag cgattgaagc gctgaatcac gcgttttata cactttgcc    4140 aaaagccaaa cgcggcaatc cgcaagtcat ttttaacttc tctattaatg tgatttctaa    4200
atcaggtacg acaactgaac ctgcaatcgc tttccgtatt ttccgcaagc ttcttgaaga    4260
gaaatacggt aaagaagaag cgaaagcgcg gatttatgca acaactgata agagcgcgg    4320 cgcattaaaa acgctttcta acgaagaagg ctttgaatca ttcgtaattc ctgacgatgt    4380
cggcggccgt tattcagttt taacagctgt aggtctcttg ccgattgctg tcagcggcgt    4440
caacattgac gacatgatga aaggcgccct ggatgcgagc aaagattttg caacatctga    4500
actggaagat aacccagcat accaatatgc ggttgttcgc aatgtccttt ataataaggg    4560
caaaacaatt gaaatgctca tcaactacga accggcgctt caatactttg cggaatggtg    4620
gaagcagctg ttcggagaaa gcgaagggaa agatgagaag gcatttatc cttcttcagc    4680 gaactattca acagaccttc attctttagg ccagtatgta caagaaggcc gcagagattt    4740
attcgaaacg gtcctgaacg tagagaagcc taaacatgaa ctgacaattg aggaagcgga    4800
taacgatctt gacggcttga actatttagc cggtaaaact gttgatttcg ttaacaaaaa    4860
agcattccaa ggtacaatgc ttgcccatac agacggaaat gttccgaact taatcgttaa    4920
cattcctgag ctgaatgcat atactttgg ataccttgta tatttcttcg aaaaagcctg    4980
cgcgatgagc ggttacctcc ttggcgtcaa tccgtttgac cagcctggtg tagaagcgta    5040
taaagtcaat atgtttgcgt tactcggcaa acctggcttt gaagagaaaa aagcagagct    5100
tgaaaaacgt ctggaagatt ataaatgagc tagcatgact ggtggacagc aaatgggtcg    5160
ggatctgtac gacgatgacg ataaggatcc ggtaccggcc gcatgccggc taatcgcgac    5220
cggttaacta gcataacccc ttggggcctc taaacgggtc ttgaggggtt ttttgctaaa    5280
ggaggaacta tatccggtcc aagaattgga gccaatcaat tcttgcggag aactgtgaat    5340
gcgcaaacca accccttggca gaacatatcc atcgcgtccg ccatctccag cagccgcacg    5400
cggcgcatct cgggccgcgt tgctggcgtt tttccatagg ctccgcccccc ctgacgagca    5460 tcacaaaaat cgacgctcaa gtcagaggtg gcgaaacccg acaggactat aaagatacca    5520
ggcgtttccc cctggaagct ccctcgtgcg ctctcctgtt ccgaccctgc cgcttaccgg    5580
atacctgtcc gcctttctcc cttcgggaag cgtggcgctt tctcatagct cacgctgtag    5640
gtatctcagt tcggtgtagg tcgttcgctc caagctgggc tgtgtgcacg aaccccccgt    5700
tcagcccgac cgctgcgcct atccggtaa ctatcgtctt gagtccaacc cggtaagaca    5760
cgacttatcg ccactggcag cagccactgg taacaggatt agcagagcga ggtatgtagg    5820
cggtgctaca gagttcttga agtggtggcc taactacggc tacactagaa ggacagtatt    5880
tggtatctgc gctctgctga agccagttac cttcggaaaa agagttggta gctcttgatc    5940
cggcaaacaa accaccgctg gtagcggtgg ttttttttgtt tgcaagcagc agattacgcg    6000
cagaaaaaaa ggatctcaag aagatccttt gatcttttct acggggtctg acgctcagtg    6060
gaacgaaaac tcacgttaag ggattttggt catgagatta tcaaaaagga tcttcaccta    6120
gatcctttta aattaaaaat gaagttttaa atcaatctaa agtatatatg agtaaacttg    6180
gtctgacagt taccaatgct taatcagtga ggcacctatc tcagcgatct gtctatttcg    6240
```

```
ttcatccata gttgcctgac tccccgtcgt gtagataact acgatacggg agggcttacc   6300
atctggcccc agtgctgcaa tgataccgcg agacccacgc tcaccggctc cagatttatc   6360
agcaataaac cagccagccg aagggccga gcgcagaagt ggtcctgcaa ctttatccgc    6420
ctccatccag tctattaatt gttgccggga agctagagta agtagttcgc cagttaatag   6480
tttgcgcaac gttgttgcca ttgctgcagg catcgtggtg tcacgctcgt cgtttggtat   6540
ggcttcattc agctccggtt cccaacgatc aaggcgagtt acatgatccc ccatgttgtg   6600
caaaaaagcg gttagctcct tcggtcctcc gatcgttgtc agaagtaagt tggccgcagt   6660
gttatcactc atggttatgg cagcactgca taattctctt actgtcatgc catccgtaag   6720
atgcttttct gtgactggtg agtactcaac caagtcattc tgagaatagt gtatgcggcg   6780
accgagttgc tcttgcccgg cgtcaacacg ggataatacc gcgccacata gcagaacttt   6840
aaaagtgctc atcattggaa aacgttcttc ggggcgaaaa ctctcaagga tcttaccgct   6900
gttgagatcc agttcgatgt aacccactcg tgcacccaac tgatcttcag catcttttac   6960
tttcaccagc gtttctgggt gagcaaaaac aggaaggcaa aatgccgcaa aaaagggaat   7020
aagggcgaca cggaaatgtt gaatactcat actcttcctt tttcaatatt attgaagcat   7080
ttatcagggt tattgtctca tgagcggata catatttgaa tgtatttaga aaaataaaca   7140
aataggggtt ccgcgcacat ttccccgaaa agtgccacct gacgtctaag aaaccattat   7200
tatcatgaca ttaacctata aaaataggcg tatcacgagg ccctttcgtc ttcaagaatt   7260
cctgttataa aaaaggatc aattttgaac tctctcccaa agttgatccc ttaacgattt    7320
agaaatccct ttgagaatgt ttatatacat tcaaggtaac cagccaacta atgacaatga   7380
ttcctgaaaa aagtaataac aaattactat acagataagt tgactgatca acttccatag   7440
gtaacaacct ttgatcaagt aagggtatgg ataataaacc acctacaatt gcaatacctg   7500
ttccctctga taaaaagctg gtaaagttaa gcaaactcat tccagcacca gcttcctgct   7560
gtttcaagct acttgaaaca attgttgata taactgtttt ggtgaacgaa agcccaccta   7620
aaacaaatac gattataatt gtcatgaacc atgatgttgt ttctaaaaga aaggaagcag   7680
ttaaaaagct aacagaaaga aatgtaactc cgatgtttaa cacgtataaa ggacctcttc   7740
tatcaacaag tatcccacca atgtagccga aaataatgac actcattgtt ccagggaaaa   7800
taattacact tccgatttcg gcagtactta gctggtgaac atctttcatc atataaggaa   7860
ccatagagac aaaccctgct actgttccaa atataattcc cccacaaaga actccaatca   7920
taaaaggtat atttttccct aatccgggat caacaaaagg atctgttact ttcctgatat   7980
gttttacaaa tatcaggaat gacagcacgc taacgataag aaaagaaatg ctatatgatg   8040
ttgtaaacaa cataaaaaat acaatgccta cagacattag tataattcct ttgatatcaa   8100
aatgaccttt tatccttact tctttctta ataatttcat aagaaacgga acagtgataa    8160
ttgttatcat aggaatgagt agaagatagg accaatgaat ataatgggct atcattccac   8220
caatcgctgg accgactcct tctcccatgg ctactatcga tccaataaga ccaaatgctt   8280
taccccctatt ttccttttgga atatagcgcg caactacaac cattacgagt gctggaaatg  8340
cagctgcacc agcccttga ataaaacgag ccataataag taaggaaaag aaagaatggc    8400
caacaaaccc aattaccgac ccgaaacaat ttattataat tccaaatagg agtaaccttt   8460
tgatgcctaa ttgatcagat agcttttcat atacagctgt tccaatggaa aaggttaaca   8520
taaaggctgt gttcacccag tttgtactcg caggtggttt attaaaatca tttgcaatat   8580
```

```
caggtaatga gacgttcaaa accatttcat ttaatacgct aaaaaaagat aaaatgcaaa    8640
gccaaattaa aatttggttg tgtcgtaaat tcgattgtga ataggatgta ttcacatttc    8700
accctccaat aatgagggca gacgtagttt atagggttaa tgatacgctt ccctctttta    8760
attgaaccct gttacattca ttacacttca taattaattc ctcctaaact tgattaaaac    8820
attttaccac atataaacta agttttaaat tcagtatttc atcacttata caacaatatg    8880
gcccgtttgt tgaactactc tttaataaaa taattttttcc gttcccaatt ccacattgca    8940
ataatagaaa atccatcttc atcggctttt tcgtcatcat ctgtatgaat caaatcgcct    9000
tcttctgtgt catcaaggtt taattttta tgtatttctt ttaacaaacc accataggag    9060
attaaccttt tacggtgtaa accttcctcc aaatcagaca aacgtttcaa attcttttct    9120
tcatcatcgg tcataaaatc cgtatccttt acaggatatt ttgcagtttc gtcaattgcc    9180
gattgtatat ccgatttata tttatttttc ggtcgaatca tttgaacttt tacatttgga    9240
tcatagtcta atttcattgc cttttccaa aattgaatcc attgttttg attcacgtag    9300 ttttctgtat tcttaaaata agttggttcc acacatacca atacatgcat gtgctgatta    9360
taagaattat ctttattatt tattgtcact tccgttgcac gcataaaacc aacaagattt    9420
ttattaattt ttttatattg catcattcgg cgaaatcctt gagccatatc tgacaaactc    9480
ttatttaatt cttcgccatc ataaacattt ttaactgtta atgtgagaaa caaccaacga    9540
actgttggct tttgtttaat aacttcagca acaaccttt gtgactgaat gccatgtttc    9600
attgctctcc tccagttgca cattggacaa agcctggatt tacaaaacca cactcgatac    9660
aactttcttt cgcctgtttc acgattttgt ttatactcta atatttcagc acaatctttt    9720
actctttcag ccttttttaaa ttcaagaata tgcagaagtt caaagtaatc aacattagcg    9780
attttctttt ctctccatgg tctcactttt ccacttttg tcttgtccac taaaacccctt    9840 gattttcat ctgaataaat gctactatta ggacacataa tattaaaaga aaccccccatc    9900 tatttagtta tttgtttggt cacttataac tttaacagat ggggttttc tgtgcaacca    9960 attttaaggg ttttcaatac tttaaaacac atacatacca acacttcaac gcacctttca   10020
gcaactaaaa taaaaatgac gttatttcta tatgtatcaa gataagaaag aacaagttca   10080
aaaccatcaa aaaaagacac cttttcaggt gctttttta ttttataaac tcattccctg   10140
atctcgactt cgttcttttt ttacctctcg gttatgagtt agttcaaatt cgtt         10194
```

<210> SEQ ID NO 3
<211> LENGTH: 27
<212> TYPE: DNA
<213> ORGANISM: artificial
<220> FEATURE:
<223> OTHER INFORMATION: tuaD gene amplification primer

<400> SEQUENCE: 3
atgaaaaaat agctgtcatt ggaacag                                         27

<210> SEQ ID NO 4
<211> LENGTH: 24
<212> TYPE: DNA
<213> ORGANISM: artificial
<220> FEATURE:
<223> OTHER INFORMATION: tuaD gene amplification primer

<400> SEQUENCE: 4
ttataaattg tcgttcccaa gtct                                            24

```
<210> SEQ ID NO 5
<211> LENGTH: 31
<212> TYPE: DNA
<213> ORGANISM: artificial
<220> FEATURE:
<223> OTHER INFORMATION: tuaD gene cloning primer

<400> SEQUENCE: 5
gctggatcca tgaaaaaata gctgtcattg g                              31

<210> SEQ ID NO 6
<211> LENGTH: 31
<212> TYPE: DNA
<213> ORGANISM: artificial
<220> FEATURE:
<223> OTHER INFORMATION: tuaD gene cloning primer

<400> SEQUENCE: 6
ctcgctagct tataaattga cgcttcccaa g                              31

<210> SEQ ID NO 7
<211> LENGTH: 28
<212> TYPE: DNA
<213> ORGANISM: artificial
<220> FEATURE:
<223> OTHER INFORMATION: Amplification primer for the introduction of a
      Shine-Dalgarno sequence in the tuaDgene

<400> SEQUENCE: 7
cgacatatga aaaatagct gtcattgg                                   28

<210> SEQ ID NO 8
<211> LENGTH: 31
<212> TYPE: DNA
<213> ORGANISM: artificial
<220> FEATURE:
<223> OTHER INFORMATION: Amplification primer for the introduction of a
      Shine-Dalgarno sequence in the tuaDgene

<400> SEQUENCE: 8
ctcgctagct tataaattga cgcttcccaa g                              31

<210> SEQ ID NO 9
<211> LENGTH: 26
<212> TYPE: DNA
<213> ORGANISM: artificial
<220> FEATURE:
<223> OTHER INFORMATION: hasA gene amplification primer

<400> SEQUENCE: 9
atgagaacat taaaaaacct cataac                                    26

<210> SEQ ID NO 10
<211> LENGTH: 25
<212> TYPE: DNA
<213> ORGANISM: artificial
<220> FEATURE:
<223> OTHER INFORMATION: hasA gene amplification primer

<400> SEQUENCE: 10
taataatttt ttacgtgttc cccag                                     25

<210> SEQ ID NO 11
<211> LENGTH: 32
<212> TYPE: DNA
<213> ORGANISM: artificial
<220> FEATURE:
```

-continued

<223> OTHER INFORMATION: hasA cloning primer

<400> SEQUENCE: 11
ggaggatcca tgagaacatt aaaaaacctc at                32

<210> SEQ ID NO 12
<211> LENGTH: 31
<212> TYPE: DNA
<213> ORGANISM: artificial
<220> FEATURE:
<223> OTHER INFORMATION: hasA cloning primer

<400> SEQUENCE: 12
cagtctagat tataataatt tttacgtgtc c                31

<210> SEQ ID NO 13
<211> LENGTH: 30
<212> TYPE: DNA
<213> ORGANISM: artificial
<220> FEATURE:
<223> OTHER INFORMATION: Cloning primer for the introduction of BsrGI e
      BamHI sites upstream and downstream the hasA and tuaDgene

<400> SEQUENCE: 13
gcttgtacat gagaacatta aaaaacctca                30

<210> SEQ ID NO 14
<211> LENGTH: 30
<212> TYPE: DNA
<213> ORGANISM: artificial
<220> FEATURE:
<223> OTHER INFORMATION: Cloning primer for the introduction of BsrGI e
      BamHI sites upstream and downstream the hasA and tuaDgene

<400> SEQUENCE: 14
agggatcctt ataaattgac gcttcccaag                30

<210> SEQ ID NO 15
<211> LENGTH: 37
<212> TYPE: DNA
<213> ORGANISM: artificial
<220> FEATURE:
<223> OTHER INFORMATION: gtaB cloning primer

<400> SEQUENCE: 15
atgtctagaa taataaggaa ggtgccttttt aaatgaa        37

<210> SEQ ID NO 16
<211> LENGTH: 39
<212> TYPE: DNA
<213> ORGANISM: artificial
<220> FEATURE:
<223> OTHER INFORMATION: gtaB cloning primer

<400> SEQUENCE: 16
ctctcgagct agcttagatt tcttctttgt ttagtaaag       39

<210> SEQ ID NO 17
<211> LENGTH: 36
<212> TYPE: DNA
<213> ORGANISM: artificial
<220> FEATURE:
<223> OTHER INFORMATION: pgi cloning primer

<400> SEQUENCE: 17
tacatatgac gcatgtacgc ttgactactc caaaag          36

```
<210> SEQ ID NO 18
<211> LENGTH: 38
<212> TYPE: DNA
<213> ORGANISM: artificial
<220> FEATURE:
<223> OTHER INFORMATION: pgi cloning primer

<400> SEQUENCE: 18
atgctagctc atttataatc ttccagacgt ttttcaag                              38
```